United States Patent
Demarest et al.

(10) Patent No.: US 11,319,370 B2
(45) Date of Patent: May 3, 2022

(54) CD200R AGONIST ANTIBODIES AND USES THEREOF

(71) Applicant: Eli Lilly and Company, Indianapolis, IN (US)

(72) Inventors: Stephen J Demarest, San Diego, CA (US); Anja Koester, San Diego, CA (US); Scott Charles Potter, San Diego, CA (US); Diana Isabel Ruiz, San Diego, CA (US); Derrick Ryan Witcher, Fishers, IN (US); Xiufeng Wu, San Diego, CA (US); Payal Mehta, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 49 days.

(21) Appl. No.: 16/567,256

(22) Filed: Sep. 11, 2019

(65) Prior Publication Data

US 2020/0087395 A1 Mar. 19, 2020

Related U.S. Application Data

(60) Provisional application No. 62/731,204, filed on Sep. 14, 2018.

(51) Int. Cl.

| | | |
|---|---|---|
| *C07K 16/28* | (2006.01) | |
| *A61K 39/395* | (2006.01) | |
| *A61P 17/00* | (2006.01) | |
| *A61P 1/00* | (2006.01) | |
| *A61P 29/00* | (2006.01) | |
| *A61K 39/00* | (2006.01) | |

(52) U.S. Cl.
CPC .... *C07K 16/2803* (2013.01); *A61K 39/39541* (2013.01); *A61P 1/00* (2018.01); *A61P 17/00* (2018.01); *A61P 29/00* (2018.01); *C07K 16/2896* (2013.01); *A61K 2039/505* (2013.01); *C07K 2317/55* (2013.01); *C07K 2317/565* (2013.01); *C07K 2317/75* (2013.01); *C07K 2317/92* (2013.01)

(58) Field of Classification Search
None
See application file for complete search history.

(56) References Cited

U.S. PATENT DOCUMENTS 8,212,008 B2  7/2012 Presta et al.

FOREIGN PATENT DOCUMENTS

WO  2015/057906 A1  4/2015

OTHER PUBLICATIONS

Holmannová et al, (Acta Medica (Hradec Králové) 2012; vol. 55; pp. 59-65).*
Prodeus et al, Molecular Therapy: Nucleic Acids vol. 12; Sep. 2018, pp. 350-358.*
Liu, The Journal of Neuroscience, 2010, 30(6):2025-2038.*
Simelyte et al., Clin Exp Immunol. 162:163-8 (2010).
Chen et al., PLoS One. 2016;11(2):e0146681. doi:10.1371/journal.pone.0146681.

* cited by examiner

*Primary Examiner* — Bridget E Bunner
*Assistant Examiner* — Fozia M Hamud
(74) *Attorney, Agent, or Firm* — Robert Sharp

(57) ABSTRACT

The present invention relates to anti-human CD200R agonist antibodies, and uses thereof for treating diseases such as atopic dermatitis, chronic spontaneous urticaria, allergy, asthma, scleroderma, IBD, SLE, MS, RA, GvHD, or psoriasis.

14 Claims, No Drawings
Specification includes a Sequence Listing.

CD200R AGONIST ANTIBODIES AND USES THEREOF

SEQUENCE LISTING

The present application includes a Sequence Listing in ASCII format. The Sequence Listing is provided as a file entitled X21772CorrectedSequenceListing created Nov. 20, 2019, which is 27423 bytes in size. The information in the electronic format of the sequence listing is incorporated herein by reference in its entirety.

The present invention is in the field of medicine. More particularly, the present invention relates to agonistic antibodies directed to CD200 Receptor (CD200R), compositions comprising such CD200R agonistic antibodies, and methods of using such CD200R agonistic antibodies for the treatment of disorders such as autoimmune disease, allergic disease, asthma, or other inflammatory disorders.

Immune checkpoint pathways may modulate both the autoimmune response and the anti-cancer immune response. In autoimmune disease therapy, promoting, i.e., agonizing, the effect of an immune-inhibitory pathway, such that the immune response is suppressed, is desirable. Conversely, in cancer therapy, inhibiting, i.e., antagonizing, the effect of an immune-inhibitory pathway, such that the immune response is derepressed (stimulated), is desirable.

CD200R is an Ig superfamily member and part of a family of checkpoint receptors that negatively regulate immune cell activation. Activation of the CD200R pathway leads to decreased cellular function, such as reduced cellular proliferation and inhibition of inflammatory cytokines. CD200R is primarily expressed on the surface of cells of the innate system, specifically of the monocytic lineage like macrophages, mast cells, dendritic cells, but also on activated T cell subsets such as T memory cells. The natural ligand for CD200R is CD200, which is more broadly expressed on multiple cell types including lymphocytes. CD200R and CD200 knockout mice have a normal phenotype, but are more prone to induced autoimmune disease (see e.g., Simelyte et al., Clin Exp Immunol. 162:163-8 (2010)). Conversely, CD200 overexpression in mice provides resistance to allogeneic transplantation and DSS-induced colitis (Chen et al., PLoS One. 2016; 11(2):e0146681. doi:10.1371/journal.pone.0146681).

Therefore, increasing CD200R mediated signaling constitutes a potential approach to manage autoimmune disorders that may lead to profound disease modification and durability of response along with key safety benefits over current immunomodulatory therapies. For example, CD200R is highly expressed in differentiated, tissue-resident cells like macrophages, mast cells, dendritic cells, and innate lymphoid cells. These cell types contribute to the pathology of diseases such as atopic dermatitis, and therefore CD200R agonist antibodies may attenuate the activity of these cells in diseases such as atopic dermatitis.

The field has struggled to deliver therapeutically effective and safe CD200R agonistic antibodies. The difficulty, at least partly, is thought to be the result of the complex cellular interactions required to achieve CD200R agonism with minimal safety concerns (e.g. without inducing cytokine release) in physiological settings.

U.S. Pat. No. 8,212,008 discloses CD200R antibodies, such as Dx182. Dx182 is a humanized IgG1 antibody that agonizes CD200R and blocks binding of CD200 to CD200R. However, Dx182 also binds to and activates cynomolgus monkey CD200RLa (cynomolgus monkey activating form) expressed in murine mast cells, and thereby induces a mast cell degranulation response in these cells via the cynomolgus CD200RLa. WO 2015/057906 also discloses CD200R agonist antibodies, such as H2RM147. H2RM147 is likely to compete with human CD200 for binding to human CD200R1.

Thus, there exists a need for alternative CD200R antibodies that 1) bind human CD200R with desirable association and dissociation rates for optimal agonist activity, 2) agonize human CD200R to achieve immunosuppressive response and in vivo efficacy, 3) display sufficient potency as an monotherapy for the treatment and/or prevention of disorders such as autoimmune disorders, allergic disease, asthma, or other inflammatory disorders, 4) do not cause significant cytokine release, 5) do not block binding of human CD200 and human CD200R, 6) do not bind CD200RLa or binds CD200RLa with low affinity. and/or 7) demonstrate low immunogenicity (i.e., sufficiently non-immunogenic in cynomolgus monkeys and/or humans) and in vivo stability, physical and chemical stability including, but not limited to, thermal stability, solubility, low self-association, and pharmacokinetic characteristics which are acceptable for development and/or use in the treatment of autoimmune disorders, allergic disease, asthma, or other inflammatory disorders.

Accordingly, the present invention provides novel anti-human CD200R agonist antibodies. The antibodies of the present invention are particularly advantageous over prior art CD200R agonist antibodies in view of at least the following properties: 1) desirable association and dissociation rates, 2) agonism of human CD200R to achieve an immunosuppressive response and in vivo efficacy, 3) sufficiently potent as an monotherapy for the treatment and/or prevention of autoimmune disorders, allergic disease, asthma, or other inflammatory disorders 4) no significant cytokine release, 5) no blocking of binding of human CD200 to human CD200R, and binding to a different epitope compared to prior art antibodies, 6) lack of binding, or binding with low affinity, the cyno CD200RLa compared to binding to human CD200R, and/or 7) low immunogenicity (i.e., sufficiently non-immunogenic in cynomolgus monkeys and/or humans) and in vivo stability, physical and chemical stability including, but not limited to, thermal stability, solubility, low self-association, and pharmacokinetic characteristics which are acceptable for development and/or use in the treatment of autoimmune disorders, allergic disease, asthma, or other inflammatory disorders.

The subject invention provides an advance over the prior art by providing compositions and methods useful in the prevention, downregulation, or amelioration of autoimmune and/or immune tolerance related disorders, allergic disease, asthma, or other inflammatory disorders, through immune checkpoint stimulation using a significantly engineered anti-human CD200R agonist antibody. The anti-human CD200R agonist antibodies of the present invention are capable of improving immune pathology or restoring immune homeostasis, preferably, through inhibition of the innate arm of the immune response, abrogation of the antigen specific immune process, and thereby directly addressing the underlying disease pathology. The use of such antibodies clinically may lead to long-term durability of the disease(s) being treated.

Accordingly, the present invention provides an antibody that binds human CD200R (SEQ ID NO: 15), comprising a heavy chain variable region (HCVR) and a light chain variable region (LCVR), wherein the HCVR comprises a HCDR1, HCDR2, and HCDR3, and the LCVR comprises a LCDR1, LCDR2, and LCDR3, wherein the amino acid sequence of the HCDR1 is given by SEQ ID NO: 1, the amino acid sequence of the HCDR2 is given by SEQ ID NO: 2, and the amino acid sequence of the HCDR3 is given by SEQ ID NO: 3, the amino acid sequence of the LCDR1 is given by SEQ ID NO: 4, the amino acid sequence of the LCDR2 is given by SEQ ID NO: 5, and the amino acid sequence of the LCDR3 is given by SEQ ID NO: 6.

In an embodiment, the present invention provides an antibody that binds human CD200R, comprising a HCVR and a LCVR, wherein the amino acid sequence of the HCVR is given by SEQ ID NO: 7 and the amino acid sequence of the LCVR is given by SEQ ID NO: 8. In some embodiments, Xaa at position 1 of SEQ ID NO: 7 is glutamine. In other embodiments, Xaa at position 1 of SEQ ID NO: 7 is pyroglutamic acid.

In an embodiment, the present invention provides an antibody that binds human CD200R, comprising a heavy chain (HC) and a light chain (LC), wherein the amino acid sequence of the HC is given by SEQ ID NO: 9 and the amino acid sequence of the LC is given by SEQ ID NO: 10. In some embodiments, Xaa at position 1 of SEQ ID NO: 9 is glutamine. In other embodiments, Xaa at position 1 of SEQ ID NO: 9 is pyroglutamic acid. In some embodiments, Xaa at position 446 of SEQ ID NO: 9 is glycine. In some embodiments, Xaa at position 446 of SEQ ID NO: 9 is absent. In a particular embodiment, Xaa at position 1 of SEQ ID NO: 9 is glutamine and Xaa at position 446 of SEQ ID NO: 9 is glycine. In another particular embodiment, Xaa at position 1 of SEQ ID NO: 9 is pyroglutamic acid and Xaa at position 446 of SEQ ID NO: 9 is glycine. In a particular embodiment, Xaa at position 1 of SEQ ID NO: 9 is glutamine and Xaa at position 446 of SEQ ID NO: 9 is absent. In another particular embodiment, Xaa at position 1 of SEQ ID NO: 9 is pyroglutamic acid and Xaa at position 446 of SEQ ID NO: 9 is absent.

In an embodiment, an antibody of the present invention does not cause significant cytokine release. In another embodiment, the antibody is a CD200R agonist antibody. In a preferred embodiment, the antibody does not cause significant cytokine release and the antibody is a CD200R agonist antibody. In some such embodiments, the antibody is an IgG4 subtype, preferably, an IgG4P. In another embodiment, the antibody binds human and cynomolgus monkey CD200R.

The present disclosure also provides a mammalian cell capable of expressing a anti-human CD200R antibody comprising: 1) a HCVR comprising a HCDR1 having the amino acid sequence of SEQ ID NO: 1, a HCDR2 having the amino acid sequence of SEQ ID NO: 2, a HCDR3 having the amino acid sequence of SEQ ID NO: 3; and 2) a LCVR comprising a LCDR1 having the amino acid sequence of SEQ ID NO: 4, a LCDR2 having the amino acid sequence of SEQ ID NO: 5, and a LCDR3 having the amino acid sequence of SEQ ID NO: 6. In some embodiments, the present disclosure provides a mammalian cell capable of expressing an anti-human CD200R antibody comprising: 1) a HCVR having the amino acid sequence of SEQ ID NO: 7; and 2) a LCVR having the amino acid sequence of SEQ ID NO: 8. In some embodiments, the present disclosure provides a mammalian cell capable of expressing a CD200R antibody comprising: 1) a heavy chain having the amino acid sequence of SEQ ID NO: 9; and 2) a light chain having the amino acid sequence of SEQ ID NO: 10. In some embodiments, the present disclosure provides that the CD200R antibody consists of two heavy chains each having the amino acid sequence of SEQ ID NO: 9, and two light chains each having the amino acid sequence of SEQ ID NO: 10.

In an embodiment, an antibody of the present invention does not cause significant cytokine release. In another embodiment, the antibody is a CD200R agonist antibody. In a preferred embodiment, the antibody does not cause significant cytokine release and the antibody is a CD200R agonist antibody. In some such embodiments, the antibody is an IgG4 subtype, preferably, an IgG4P. In another embodiment, the antibody binds human and cynomolgus monkey CD200R.

The present disclosure also provides a process for producing an anti-human CD200R antibody, comprising: a) cultivating a mammalian cell capable of expressing the antibody, wherein the antibody comprises: 1) a HCVR comprising a HCDR1 having the amino acid sequence of SEQ ID NO: 1, a HCDR2 having the amino acid sequence of SEQ ID NO: 2, a HCDR3 having the amino acid sequence of SEQ ID NO: 3; and 2) a LCVR comprising a LCDR1 having the amino acid sequence of SEQ ID NO: 4, a LCDR2 having the amino acid sequence of SEQ ID NO: 5, and a LCDR3 having the amino acid sequence of SEQ ID NO: 6; and b) recovering the antibody. In some embodiments, the present disclosure provides a process for producing a CD200R antibody, comprising: a) cultivating a mammalian cell capable of expressing the antibody, wherein the antibody comprises: 1) a HCVR having the amino acid sequence of SEQ ID NO: 7; and 2) a LCVR having the amino acid sequence of SEQ ID NO: 8; and b) recovering the antibody. In some embodiments, the present disclosure provides a process for producing an anti-human CD200R antibody, comprising: a) cultivating a mammalian cell capable of expressing the antibody, wherein the antibody comprises: 1) a heavy chain having the amino acid sequence of SEQ ID NO: 9; and 2) a light chain having the amino acid sequence of SEQ ID NO: 10; and b) recovering the antibody. In some embodiments, the present disclosure provides a process for producing an anti-human CD200R antibody, comprising: a) cultivating a mammalian cell capable of expressing the antibody, wherein the antibody consists of two heavy chains having the amino acid sequence of SEQ ID NO: 9 and two light chains having the amino acid sequence of SEQ ID NO: 10; and b) recovering the antibody.

In an embodiment, an antibody of the present invention does not cause significant cytokine release. In another embodiment, the antibody is a CD200R agonist antibody. In a preferred embodiment, the antibody does not cause significant cytokine release and the antibody is a CD200R agonist antibody. In some such embodiments, the antibody is an IgG4 subtype, preferably, an IgG4P. In another embodiment, the antibody binds human and cynomolgus monkey CD200R.

The present disclosure also provides the CD200R antibody produced by the aforementioned processes. The present disclosure also provides a pharmaceutical composition comprising the CD200R antibody produced by the aforementioned processes and an acceptable carrier, diluent, or excipient.

The present disclosure also provides a DNA molecule comprising a polynucleotide having the sequence of SEQ ID NO: 12. The present disclosure also provides a DNA molecule comprising a polynucleotide having the sequence of SEQ ID NO: 13. The present disclosure also provides a DNA molecule comprising a polynucleotide having the sequence of SEQ ID NO: 12 and SEQ ID NO: 13. The present disclosure also provides a DNA molecule comprising a polynucleotide that encodes the antibody HC whose amino acid sequence is the sequence of SEQ ID NO: 9. In an embodiment, the DNA molecule that encodes the antibody HC is given by SEQ ID NO: 12. The present disclosure also provides a DNA molecule comprising a polynucleotide that encodes the antibody LC whose amino acid sequence is the sequence of SEQ ID NO: 10. In an embodiment, the DNA molecule that encodes the antibody LC is given by SEQ ID NO: 13.

The present disclosure also provides a mammalian cell comprising a DNA molecule comprising a polynucleotide having the sequence of SEQ ID NO: 12. The present disclosure also provides a mammalian cell comprising a DNA molecule comprising a polynucleotide having the sequence of SEQ ID NO: 13. The present disclosure also provides a mammalian cell comprising a DNA molecule comprising a polynucleotide having the sequence of SEQ ID NO: 12 and SEQ ID NO: 13.

The present invention also provides a pharmaceutical composition comprising an antibody of the present invention.

The present invention also provides a method of treating a patient having a disease, wherein the disease is an autoimmune disease, allergic disease, asthma, or other inflammatory disorders, comprising administering to a patient in need thereof, an effective amount of an antibody of the present invention.

The present invention also provides an antibody of the present invention for use in therapy.

The present invention also provides an antibody of the present invention for use in treating a disease, wherein the disease is an autoimmune disease, allergic disease, asthma, or other inflammatory disorders.

The present invention also provides use of an antibody of the present invention for the manufacture of a medicament for the treatment of a disease, wherein the disease is an autoimmune disease, allergic disease, asthma, or other inflammatory disorders.

In an embodiment, the disease is an autoimmune disease. In another embodiment, the disease is an allergic disease. In another embodiment, the disease is asthma. In some embodiments, the disease is chronic idiopathic urticaria (also referred to herein as chronic spontaneous urticaria (CSU)), celiac disease (including, but not limited to, refractory celiac disease type II), allergy, chronic allergic disease, food allergies, eosinophilic esophagitis, macrophage activation syndrome (MAS), asthma, scleroderma, pemphigus, irritable bowel disease (IBD), systemic lupus erythematosus (SLE), multiple sclerosis (MS), rheumatoid arthritis (RA), graft versus host disease (GvHD), psoriasis, mastocytosis, inflammatory skin disease, or atopic dermatitis. In other embodiments, the disease is allergic contact dermatitis, seasonal allergies, anaphylaxis treatment and prevention, bullous pemphigoid and other autoimmune blistering diseases, autoimmune hepatitis, primary sclerosing cholangitis, primary biliary cirrhosis, idiopathic pulmonary fibrosis, myasthenia gravis, vasculitis, and myositis. In a particular embodiment, the chronic allergic disease is hay fever or allergic rhinitis. In a preferred embodiment, the disease is atopic dermatitis.

The present invention provides an antibody that binds human CD200R, wherein the antibody is a CD200R agonist antibody and wherein the antibody does not cause significant cytokine release. In an embodiment, the antibody demonstrates CD200R agonism and lack of significant cytokine release similar to the CD200R agonism and lack of significant cytokine release as demonstrated by Antibody I-4P. In an embodiment, the CD200R agonist antibody does not cause significant cytokine release compared to a wild-type (no mutations in the Fc portion) IgG1 antibody (which does cause significant cytokine release, especially release of IFN-γ). In a particular embodiment, the present invention provides a CD200R agonist antibody, wherein the antibody does not cause significant cytokine release compared to a wild-type IgG1 antibody having the same CDRs as the CD200R agonist antibody. In an embodiment, a significant cytokine release is detected by comparing the amount of cytokine present in blood samples incubated with the antibody and the amount of cytokine present in blood samples without incubation with the antibody and determining the presence of significant cytokine release if the amount of cytokine present in blood sample incubated with the antibody is at least three-fold higher than the amount of cytokine present in blood sample with no antibody.

In an embodiment, the antibody comprises a HCVR and a LCVR, wherein the HCVR comprises a HCDR1, HCDR2, and HCDR3, and the LCVR comprises a LCDR1, LCDR2, and LCDR3, wherein the amino acid sequence of the HCDR1 is given by SEQ ID NO: 1, the amino acid sequence of the HCDR2 is given by SEQ ID NO: 2, and the amino acid sequence of the HCDR3 is given by SEQ ID NO: 3, the amino acid sequence of the LCDR1 is given by SEQ ID NO: 4, the amino acid sequence of the LCDR2 is given by SEQ ID NO: 5, and the amino acid sequence of the LCDR3 is given by SEQ ID NO: 6. In an embodiment, the antibody comprises a HCVR and a LCVR, wherein the amino acid sequence of the HCVR is given by SEQ ID NO: 7 and the amino acid sequence of the LCVR is given by SEQ ID NO: 8.

The present invention provides an antibody of the present invention that binds at least one, at least two, at least three, at least four, or all of Fcγ RI, Fcγ RIIA_131H, Fcγ RIIA_131R, Fcγ RIIb, and Fcγ RIIIA_158V.

In an embodiment, the antibody binds Fcγ RI with a binding affinity of about 70 pM to about 500 pM. In another embodiment, the antibody binds Fcγ RIIA_131H with a binding affinity of about 2 µM to about 5 µM. In another embodiment, the antibody binds Fcγ RITA 131R with a binding affinity of about 1 µM to about 5 µM. In another embodiment, the antibody binds Fcγ RIIb with a binding affinity of about 1 µM to about 4 µM. In another embodiment, the antibody binds Fcγ RIIIA_158V with a binding affinity of about 1 µM to about 6 µM. In another embodiment, the antibody further binds Fcγ RIIIA_158F with a binding affinity of greater than 9 µM.

In an embodiment, the binding affinities of the antibody to the receptor are about 70 pM to about 500 pM to Fcγ RI, about 2 µM to about 5 µM to Fcγ RIIA_131H, about 1 µM to about 5 µM to Fcγ RIIA_131R, about 1 µM to about 4 µM to Fcγ RIIb, about 1 µM to about 6 µM to Fcγ RIIIA_158V, and greater than 9 µM to Fcγ RIIIA_158F. In a more particular embodiment, the binding affinities of the antibody to the receptor are about 400 pM to Fcγ RI, about 4 µM to Fcγ RIIA_131H, about 2 µM to Fcγ RITA 131R, about 2 µM to Fcγ RIIb, about 4 µM to Fcγ RIIIA_158V, and greater than 10 µM to Fcγ RIIIA_158F. In a further embodiment, the antibody does not bind C1q. In some embodiments, the binding affinity is determined by Surface Plasmon Resonance at 25° C. In other embodiments, binding to C1q is determined by ELISA.

As used herein, "CD200R" refers to the CD200 receptor. As used herein, "hCD200R" or "human CD200R" refers to a wild-type human CD200R, and, preferably, to a wild-type human CD200R that has the amino acid sequence set forth in SEQ ID NO: 15.

The terms "cyno", "cynomolgus" or "cynomolgus monkey" are used interchangeably, herein. When used in reference to a CD200R polypeptide, unless otherwise stated, it is intended that the terms refer to wild-type cynomolgus monkey CD200R, and, preferably, a wild-type cynomolgus monkey CD200R that has the amino acid sequence set forth in SEQ ID NO: 16. The terms "CD200RLa" or "activating form" refer to a cynomolgus monkey CD200R that has the amino acid sequence set forth in SEQ ID NO: 17. CD200RLa is a close homologue of human CD200R but with the opposite (activating) activity. Therefore, a preferred CD200R agonist antibody binds CD200RLa with a significantly reduced affinity compared to antibody binding to CD200R.

As used herein, "human CD200R agonist antibody" or "anti-human CD200R agonist antibody" refers to an antibody that binds to human CD200R, and when administered in vitro or in vivo, results in an achieved immunosuppressive response such as at least one significantly lessened desired activity such as a desired reduction in IL-8 production. As used herein, the terms "production" and "secretion," as they relate to cytokines, are used interchangeably.

The term "antibody" as used herein refers to an engineered, non-naturally occurring polypeptide complex having two heavy chains (HC) and two light chains (LC) such that the heavy chains and the light chains are interconnected by disulfide bonds, wherein the antibody is an IgG isotype antibody. Each heavy chain is comprised of an N-terminal HCVR and a heavy chain constant region. Each light chain is comprised of an N-terminal LCVR and a light chain constant region. When expressed in certain biological systems, antibodies are glycosylated in the Fc region. Typically, glycosylation occurs in the Fc region of the antibody at a highly conserved N-glycosylation site. N-glycans typically attach to asparagine. Antibodies may be glycosylated at other positions as well.

Antibodies of the present invention may be an IgG1 or IgG4 antibody. Preferably, antibodies of the present invention are IgG4 antibodies. An IgG4 antibody may have an S228P mutation within the HC (i.e., IgG4P), which is known to eliminate half-antibody formation common for the human IgG4 subclass.

The constant region of the heavy chains contains CH1, CH2, and CH3 domains. CH1 comes after the HCVR; the CH1 and HCVR form the heavy chain portion of an antigen-binding (Fab) fragment, which is the part of an antibody that binds antigen(s). CH2 comes after the hinge region and before CH3. CH3 comes after CH2 and is at the carboxy-terminal end of the heavy chain. The constant region of the light chains contains one domain, CL. CL comes after the LCVR; the CL and LCVR form the light chain portion of a Fab.

The HCVR and LCVR regions of an antibody of the present invention can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. The Kabat CDR definition (Kabat, et al., Ann. NY Acad. Sci. 190:382-93 (1971); Kabat et al., Sequences of Proteins of Immunological Interest, Fifth Edition, U.S. Department of Health and Human Services, NIH Publication No. 91-3242 (1991)) is based upon antibody sequence variability. The Chothia CDR definition (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)) is based on three-dimensional structures of antibodies and topologies of the CDR loops. The Chothia CDR definitions are identical to the Kabat CDR definitions with the exception of HCDR1 and HCDR2. The North CDR definition (North et al., "A New Clustering of Antibody CDR Loop Conformations", Journal of Molecular Biology, 406, 228-256 (2011)) is based on affinity propagation clustering with a large number of crystal structures. For the purposes of the present invention, assignment of amino acids to CDR domains within the LCVR and HCVR regions of the antibodies of the present invention is based on the well-known Kabat numbering convention and North numbering convention. In the case of the light chain CDRs of the antibodies of the present invention, the North CDR definitions are used. In the heavy chain, both HCDR1 and HCDR3 also use the North definition. HCDR2 uses a hybrid of North and Kabat definitions. The North definition is used to identify the starting N-terminal site while Kabat is used to define the last position.

The present invention contemplates that the antibodies of the present invention are human or humanized antibodies. In the context of monoclonal antibodies, the terms "human" and "humanized" are well-known to those of ordinary skill in the art (Weiner L J, J. Immunother. 2006; 29: 1-9; Mallbris L, et al., J. Clin. Aesthet. Dermatol. 2016; 9: 13-15).

A DNA molecule of the present invention is a DNA molecule that comprises a non-naturally occurring polynucleotide sequence encoding a polypeptide having the amino acid sequence of at least one of the polypeptides in an antibody of the present invention (e.g., heavy chain, light chain, variable heavy chain, and variable light chain).

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained, e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region. Preferably, for antibodies of the present invention, the light chain constant region is a kappa constant region.

The polynucleotides of the present invention can be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibodies of the present invention can readily be produced in mammalian cells, non-limiting examples of which includes CHO, NS0, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed to purify proteins, including, but not limited to, antibodies and such methods are known in the art.

An antibody of the present invention, or a pharmaceutical composition comprising the same, may be administered by parenteral routes, non-limiting examples of which are subcutaneous administration and intravenous administration. An antibody of the present invention may be administered to a patient with pharmaceutically acceptable carriers, diluents, or excipients in single or multiple doses. Pharmaceutical compositions of the present invention can be prepared by methods well known in the art (e.g., Remington: The Science and Practice of Pharmacy, 22nd ed. (2012), A. Loyd et al., Pharmaceutical Press) and comprise an antibody, as disclosed herein, and one or more pharmaceutically acceptable carriers, diluents, or excipients.

As used herein, the term "autoimmune disease" or "autoimmune disorder" are used interchangeably and refer to undesirable conditions that arise from an inappropriate or unwanted immune reaction against self-cells and/or tissues or transplanted cells and/or tissues. The term "autoimmune disease" or "autoimmune disorder" is meant to include such conditions, whether they be mediated by humoral or cellular immune responses. "Allergy" (or "allergic disease") is a T helper 2 (TH2)-driven disease that develops primarily from activity of TH2 cells. Exemplary diseases contemplated to be treated by the antibodies of the invention described herein include chronic idiopathic urticaria, celiac disease (including, but not limited to, refractory celiac disease type II), allergy, chronic allergic disease (such as hay fever or allergic rhinitis), food allergies, eosinophilic esophagitis, MAS, asthma, scleroderma, and also pemphigus, IBD, SLE, MS, RA, GvHD, psoriasis, mastocytosis, inflammatory skin disease, and atopic dermatitis. In other embodiments, the disease contemplated to be treated by the antibodies of the invention described herein include is allergic contact dermatitis, seasonal allergies, anaphylaxis treatment and prevention, bullous pemphigoid and other autoimmune blistering diseases, autoimmune hepatitis, primary sclerosing cholangitis, primary biliary cirrhosis, idiopathic pulmonary fibrosis, myasthenia gravis, vasculitis, and myositis.

The terms "chronic idiopathic urticaria" and "chronic spontaneous urticaria (CSU)" are used interchangeably herein.

As used herein, the term "innate immunity" includes the arm of the immune response which, in contrast to the adaptive arm of the immune response, is required to initiate and maintain an adaptive immune response (antibody and T cell responses).

The term "treating" (or "treat" or "treatment") refers to slowing, interrupting, arresting, alleviating, stopping, reducing, or reversing the progression or severity of an existing symptom, disorder, condition, or disease.

"Effective amount" means the amount of an anti-human CD200R agonist antibody of the present invention or pharmaceutical composition comprising such an antibody that will elicit the biological or medical response of or desired therapeutic effect on a tissue, system, animal, mammal, or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects. Such benefit includes any one or more of: an increased immune tolerance of transplanted organs; stabilized autoimmune disease or disorder; or improving signs or symptoms of an autoimmune disorder, etc. An effective amount can be readily determined by one skilled in the art, by the use of known techniques, and by observing results obtained under analogous circumstances. An effective amount of an anti-human CD200R agonist antibody of the present invention may be administered in a single dose or in multiple doses. Furthermore, an effective amount of an antibody of the invention may be administered in multiple doses of amounts that would be less than an effective amount if not administered more than once. In determining the effective amount for a patient, a number of factors are considered by the attending medical practitioner, including, but not limited to: the patient's size (e.g., weight or mass), body surface area, age, and general health; the specific disease or disorder involved; the degree of, or involvement, or the severity of the disease or disorder; the response of the individual patient; the particular compound administered; the mode of administration; the bioavailability characteristics of the preparation administered; the dose regimen selected; the use of concomitant medication; and other relevant circumstances known to medical practitioners. A weekly, every two weeks, monthly, or quarterly parenteral (including, but not limited to, subcutaneous, intramuscular, and/or intravenous) dose can be, for example, from about 50 mg to about 500 mg, from about 75 mg to about 500 mg, from about 100 mg to about 500 mg, from about 125 mg to about 500 mg, from about 250 mg to about 500 mg, from about 300 mg to about 500 mg, from about 350 mg to about 500 mg, from about 400 mg to about 500 mg, from about 450 mg to about 500 mg, from about 50 mg to about 400 mg, from about 75 mg to about 400 mg, from about 100 mg to about 400 mg, from about 125 mg to about 400 mg, from about 250 mg to about 400 mg, from about 300 mg to about 400 mg, from about 350 mg to about 400 mg, from about 50 mg to about 300 mg, from about 75 mg to about 300 mg, from about 100 mg to about 300 mg, from about 125 mg to about 300 mg, from about 150 mg to about 300 mg, from about 175 mg to about 300 mg, from about 200 mg to about 300 mg, from about 250 mg to about 300 mg, from about 50 mg to about 250 mg, from about 75 mg to about 250 mg, from about 100 mg to about 250 mg, from about 125 mg to about 250 mg, from about 150 mg to about 250 mg, from about 175 mg to about 250 mg, from about 200 mg to about 250 mg, from about 75 mg to about 250 mg, from about 50 mg to about 200 mg, from about 75 mg to about 200 mg, from about 100 mg to about 200 mg, from about 125 mg to about 200 mg, from about 150 mg to about 200 mg, from about 175 mg to about 200 mg, from about 50 mg to about 175 mg, from about 75 mg to about 175 mg, from about 100 mg to about 175 mg, from about 125 mg to about 175 mg, or from about 150 mg to about 175 mg. A weekly, every two week, monthly, or quarterly parenteral (including, but not limited to, subcutaneous, intramuscular, and/or intravenous) dose can be from about 0.5 mg/kg to about 10 mg/kg, from about 1 mg/kg to about 10 mg/kg, from about 2 mg/kg to about 10 mg/kg from about 3 mg/kg to about 10 mg/kg, from about 4 mg/kg to about 10 mg/kg, from about 5 mg/kg to about 10 mg/kg, from about 6 mg/kg to about 10 mg/kg, from about 7 mg/kg to about 10 mg/kg from about 8 mg/kg to about 10 mg/kg, from about 1 mg/kg to about 8 mg/kg, from about 2 mg/kg to about 8 mg/kg, from about 3 mg/kg to about 8 mg/kg, from about 4 mg/kg to about 8 mg/kg, from about 5 mg/kg to about 8 mg/kg, from about 6 mg/kg to about 8 mg/kg, from about 1 mg/kg to about 6 mg/kg, from about 2 mg/kg to about 6 mg/kg, from about 3 mg/kg to about 6 mg/kg, from about 4 mg/kg to about 6 mg/kg, from about 5 mg/kg to about 6 mg/kg, from about 1 mg/kg to about 5 mg/kg, from about 2 mg/kg to about 5 mg/kg, from about 3 mg/kg to about 5 mg/kg, from about 4 mg/kg to about 5 mg/kg, from about 1 mg/kg to about 4 mg/kg, from about 2 mg/kg to about 4 mg/kg, from about 3 mg/kg to about 4 mg/kg, from about 3.5 mg/kg to about 5 mg/kg, or about 4 mg/kg to about 5 mg/kg.

However, doses below or above the doses mentioned herein are also envisioned, especially considering dosage considerations known to those skilled in the art and/or described herein. Progress of the patient being treated may be monitored by periodic assessment, and the dose adjusted accordingly if necessary.

As used herein, the term "effective response" of a patient or a patient's responsiveness to treatment refers to the clinical or therapeutic benefit imparted to a patient upon administration an antibody of the present disclosure. Such benefit includes any one or more of the following: an increased immune tolerance of transplanted organs; stabilized autoimmune disease or disorder; or improving signs or symptoms of an autoimmune disorder, etc.

As used herein, "significant cytokine release" refers to a significant increase in measurable cytokines that can be detected by methods known to persons of ordinary skill. For example, significant cytokine release may be detected in human blood samples by ELISA, wherein cytokine levels from unstimulated blood are compared to cytokine levels with blood incubated with antibody. In some such studies, for example, a significant cytokine release may be detected if the levels of IFN-γ are at least three-fold higher in blood incubated with antibody compared to levels in unstimulated blood.

A potential advantage of methods disclosed herein is the possibility of producing marked and/or prolonged relief in a patient suffering from an autoimmune disorder, allergic disease, asthma, or other inflammatory disorders, with an acceptable safety profile including acceptable tolerability, toxicities and/or adverse events, so that the patient benefits from the treatment method overall. The efficacy of the treatment of the present disclosure can be measured by various endpoints that are commonly used in evaluating treatments for various autoimmune disorders including, but not limited to, American College of Rheumatology (ACR) 20, ACR50, ACR70, Psoriasis Area and Severity Index (PASI) 50, PASI75, PASI90, PASI100, Systemic Lupus Erythematosus Disease Activity Index (SLEDAI). Various other approaches to determining efficacy of any particular therapy of the present invention can be optionally employed, including, for example, immune cell activation markers, measures of inflammation, cell-cycle dependent biomarkers measurement visualization, and/or measurement of response through pain assessments.

EXAMPLE: ANTIBODY EXPRESSION AND PURIFICATION

Anti-human CD200R agonist antibodies of the present invention can be expressed and purified essentially as follows. An appropriate host cell, such as HEK 293 or CHO, can be either transiently or stably transfected with an expression system for secreting antibodies using an optimal predetermined HC:LC vector ratio (such as 1:3 or 1:2) or a single vector system encoding both the HC and the LC. Clarified media, into which the antibody has been secreted, may be purified using any of many commonly-used techniques. For example, the medium may be conveniently applied to a Mab Select® column (GE Healthcare), or KappaSelect column (GE Healthcare) for Fab fragment, that has been equilibrated with a compatible buffer, such as phosphate buffered saline (pH 7.4). The column may be washed to remove nonspecific binding components.

The bound antibody may be eluted, for example, by pH gradient (such as 20 mM Tris buffer, pH 7.0 to 10 mM sodium citrate buffer, pH 3.0, or phosphate buffered saline pH 7.4 to 100 mM glycine buffer, pH 3.0). Antibody fractions may be detected, such as by SDS-PAGE, and then may be pooled. Further purification is optional, depending on intended use. The antibody may be concentrated and or sterile filtered using common techniques. Soluble aggregate and multimers may be effectively removed by common techniques, including size exclusion, hydrophobic interaction, ion exchange, multimodal, or hydroxyapatite chromatography. The purity of the antibody after these chromatography steps is between about 95% to about 99%.

Notably, the C-terminal glycine of Antibody I-4P or the C-terminal lysine of Antibody I-IgG1 may be truncated post-translationally. Additionally, the N-terminal glutamine of Antibody I-4P or Antibody I-IgG1 may be converted to pyroglutamic acid.

The product may be held refrigerated, immediately frozen at −70° C., or may be lyophilized. Amino acid SEQ ID NOs for exemplified humanized antibodies of the present invention are shown below in Table 1.

TABLE 1

Amino acid sequences of exemplified anti-human CD200R agonist antibodies.
Antibody SEQ ID NOs

| Antibody | HCDR1 | HCDR2 | HCDR3 | LCDR1 | LCDR2 | LCDR3 |
|---|---|---|---|---|---|---|
| Antibody I | SEQ ID NO: 1 | SEQ ID NO: 2 | SEQ ID NO: 3 | SEQ ID NO: 4 | SEQ ID NO: 5 | SEQ ID NO: 6 |

| Antibody | HCVR | LCVR |
|---|---|---|
| Antibody I | SEQ ID NO: 7 | SEQ ID NO: 8 |

| Antibody | HC | LC |
|---|---|---|
| Antibody I-4P | SEQ ID NO: 9 | SEQ ID NO: 10 |

EXAMPLE: ANTIBODY I-4P BINDS HUMAN AND CYNOMOLGUS MONKEY CD200R

Surface Plasmon Resonance (SPR) at 37° C. is performed to determine the binding kinetics and affinity of Antibody I-4P to human CD200R, cynomolgus monkey CD200R, and cynomolgus monkey CD200RLa (herein also referred to as the cynomolgus monkey "activating form").

Biacore® T100 instrument (GE Healthcare, Piscataway, N.J.), Biacore reagents and Scrubber2 Biacore® Evaluation Software (Biologics 2008) are used for the SPR analysis of Antibody I-4P binding. A CM4 chip (Biacore P/N BR-1006-68) is prepared using the manufacturer's EDC/NHS amine coupling method (Biacore P/N BR-1000-50). Briefly, the surfaces of all 4 flow cells (FC) are activated by injecting a 1:1 mixture of EDC/NHS for 7 minutes at 10 µL/minute. Protein A (Calbiochem P/N 539202) is diluted to 100 µg/mL in 10 mM acetate, pH 4.5 buffer and immobilized for approximately 400 RU onto all 4 flow cells by 7 minute injection at a flow rate of 10 µL/minute. Un-reacted sites are blocked with a 7-minute injection of ethanolamine at 10 µL/minute. Injections of 2×10 µL of glycine pH 1.5 are used to remove any non-covalently associated protein. Running buffer is 1× HBS EP+(Biacore P/N BR-1006-69).

Human, cynomolgus monkey (cyno), and cynomolgus monkey activating CD200 receptors are purified using IMAC and size exclusion chromatography. Mouse CD200R is generated by Factor Xa cleavage from a mouse CD200R Fc fusion protein made in house. The final polishing step for the mouse CD200R receptor is size exclusion chromatography.

For human and cyno CD200R binding, antibodies are diluted to 2.5 µg/mL in running buffer, and approximately 150 RU of Antibody I-4P is captured in flow cells 2 through 4 (RUcaptured). FC1 is the reference flow cell; therefore, no antibody is captured in FC1. Human and cyno CD200R are diluted to 500 nM in running buffer and then two-fold serially diluted in running buffer to 3.9 nM. Duplicate injections of each concentration are injected over all FC's at 50 µL/minute for 250 seconds followed by a 1200 second dissociation phase. Regeneration is performed by injecting 15 µL of 10 mM glycine pH 1.5 at 30 µL/minute twice over all FC's. Reference-subtracted data is collected as FC2-FC1, FC3-FC1, and FC4-FC1. The measurements are obtained at 37° C. The affinity ($K_D$) is calculated using a "1:1 (Langmuir) binding" model in BIA Evaluation.

For cyno activating CD200R binding, antibodies are diluted to 2.5 µg/mL in running buffer, and approximately 150 RU of Antibody I-4P is captured in flow cells 2 through 4 (RUcaptured). FC1 is the reference flow cell. Cyno activating CD200R is diluted to 8.1 µM in running buffer and then 2 fold serially diluted in running buffer to 63.2 nM. Duplicate injections of each concentration are injected over all FC's at 50 µL/minute for 250 seconds followed by a 1200 second dissociation phase. Regeneration is performed by injecting 15 µL of 10 mM glycine pH 1.5 at 30 µL/min twice over all FC's. Reference subtracted data is collected as FC2 FC1, FC3 FC1, and FC4-FC1. The measurements are obtained at 37° C. The affinity ($K_D$) is calculated using the steady state equilibrium analysis with the Scrubber 2 Biacore® Evaluation Software.

For mouse CD200R binding, antibodies are diluted to 2.5 µg/mL in running buffer, and approximately 150 RU of Antibody I-4P is captured in flow cells 2 through 4 (RUcaptured). FC1 is the reference flow cell. Mouse CD200R is diluted to 10 µM in running buffer and then 2 fold serially diluted in running buffer to 78 nM. Duplicate injections of each concentration are injected over all FC's at 50 µL/minute for 250 seconds followed by a 1200 second dissociation phase. Regeneration is performed by injecting 15 µL of 10 mM glycine pH 1.5 at 30 µL/min twice over all FC's. Reference subtracted data are collected as FC2 FC1, FC3 FC1, and FC4-FC1. The measurements are obtained at 37° C. The affinity ($K_D$) was calculated using the steady state equilibrium analysis with the Scrubber 2 Biacore® Evaluation Software.

Following procedures essentially as described above, the following data were obtained. As shown in Table 2, Antibody I-4P binds human CD200R and cynomolgus monkey CD200R with an affinity in the nM range, and Antibody I-4P binds the CD200RLa activating receptor with an affinity in the µM range. Antibody I-4P binds mouse CD200R with an affinity of >10 µM.

TABLE 2

Affinity of Antibody I-4P to Human, Cyno, Cyno Activating, and mouse CD200 Receptors Measured Using Surface Plasmon Resonance (SPR) at 37° C.

| | Receptor | Average $K_D$ | Std. Dev. |
|---|---|---|---|
| Antibody I-4P | Human | 5.6 nM | 1.2 |
| | Cynomolgus monkey | 2.3 nM | 0.1 |
| | Cynomolgus monkey activating | 2.5 µM | 0.4 |
| | *Mouse CD200R | >10 µM | | n = Assay was performed three times;
*n = 1 time assayed

These data demonstrate that Antibody I-4P binds the CD200RLa activating receptor and mouse CD200R with reduced affinity compared to Antibody I-4P affinity to human CD200R and cynomolgus monkey CD200R.

Despite substantial engineering to overcome significant problems associated with lack of cross-reactivity between human and cyno CD200R, isomerization under stressed conditions (driven by primarily by an aspartic acid residue in LCDR1 (LC D28)), and a non-native disulfide bond between HC CDR1 and CDR2, Antibody I-4P demonstrated a favorable binding profile. For instance, a heavy chain and light chain CDR residue saturation mutagenesis procedure using mammalian cell expression was used to determine CDR changes that closed the affinity gap between human and cyno CD200R. This procedure was also used to find a residue replacement for LC D28 without compromising affinity. A second CDR library was screened using a phage-based process, which led to the discovery of non-predicted and non-germline replacement residues for the non-native disulfide without compromising antigen binding affinity.

EXAMPLE: IN VITRO BINDING OF ANTIBODY I-4P TO CD200R EXPRESSED IN CELLS

CD200R is a member of the "paired receptor family", which means that a close homologue with opposite, activating activity exists. This form has not been identified in humans, but low level mRNA transcripts have been described in whole blood and testis of cynomolgus monkeys (herein referred to the cynomolgus monkey "activating form" or "cynomolgus monkey CD200RLa"). Therefore, the cynomolgus monkey activating form could present a safety concern during toxicology studies in cynomolgus monkeys.

To determine if Antibody I-4P binds to cell-expressed, membrane-bound CD200R from cynomolgus monkey, human, and the activating form cynomolgus CD200RLa, flow cytometry is used. CHO cells are transfected with human CD200R (SEQ ID NO: 15), cynomolgus monkey CD200R (SEQ ID NO: 16), or the cynomolgus monkey activating form (SEQ ID NO: 17) and are selected for high expression. Cells ($2^e5$) are suspended in $1^e6/50$ µL in PBS for each cell line and FL4 dye (MultiCyt® Proliferation and Encoder FL4 dye) is added. The FL4 dye is diluted 1:5000 for cells expressing human and cyno CD200R, 1:700 for cells expressing the cynomolgus monkey activating form, and 1:50 for untransfected cells. The dye is mixed with the cells and the mixture is incubated at 4° C. for 30 minutes in the dark. The cells are washed twice with 10 mL of PBS and spun down at 1200 RPM for 5 minutes. The cells are then mixed in FACS buffer at $8^e5$ cells/50 µL/well.

The cells are incubated for 30 minutes at room temperature with antibody titrations made in FACS buffer. The cells are washed once with FACS buffer and 100 of PE-conjugated anti human-Fc antibody at a 1:1000 dilution is added to each well for 15 minutes in the dark at 4° C. Cells are washed three times and then resuspended in 150 µL of FACS buffer. Sytox blue (2 µL/well) is added, cells are transferred to a FACS plate, and run on a Fortessa LSRII cytometry instrument (BD Biosciences). Data is analyzed using FlowJo (FlowJo, LLC) software.

Following procedures essentially as described above, the following data were obtained. Antibody I-4P binds to cynomolgus monkey CD200R and human CD200R. Antibody I-4P binds to the cynomolgus monkey activating form similar to binding to untransfected control cells. These data demonstrate that there is no binding of Antibody I-4P to the cynomolgus monkey activating form; therefore, there may be a reduced safety concern during toxicology studies in cynomolgus monkeys.

EXAMPLE: ANTIBODY I-4P IS A CD200R AGONIST

To demonstrate the agonist activity of Antibody I-4P, a human monocyte cell line U937 (ATCC, CRL1539.2), is transfected with the cDNA for human CD200R. Cytokine production, including IL-8, from these cells can be induced by immune complexes (IC) that bind and activate Fcγ Receptors. For IC stimulation, human IgG1 isotype control antibody is coated to a high-binding plate overnight. The next day, $4 \times 10^5$ CD200R-expressing U937 cells/well are incubated with different concentrations of Antibody I-4P for 1 hour on ice before added to the pre-coated plate for IC stimulation and incubated at 37° C. for 24 hours. After 24 hours the cells are spun down, the supernatant is removed, and the IL-8 concentration measured using MSD kit (Mesoscale Diagnostics).

Following procedures essentially as described above, the following data were obtained. As shown in Table 3, the reduction of IC-induced IL-8 with Antibody I-4P as percent inhibition compared to isotype control at the corresponding concentration. The relative $IC_{50}$ is based on a four parameter logistic fit of the slope of percent inhibition over concentration. The average $IC_{50}$ from 3 independent experiments was determined to be 0.2 µg/mL±0.02 µg/mL.

TABLE 3

Concentration-dependent inhibition of immune-complex induced IL-8 secretion in cells expressing human CD200R.

| Antibody I-4P (µg/ml) | average % IL-8 inhibition | SEM |
|---|---|---|
| 0.01 | −2.0 | 3.1 |
| 0.03 | 2.3 | 2.9 |
| 0.1 | 14.0 | 6.0 |
| 0.3 | 24.0 | 4.2 |
| 1 | 47.1 | 2.8 |
| 3 | 55.7 | 2.9 |
| 10 | 67.8 | 3.3 |
| 30 | 76.2 | 4.0 |

These data demonstrate that Antibody I-4P is able to inhibit IC-induced IL-8 production in a concentration-dependent manner.

The ability of CD200R agonist antibodies with different isotype backbones to agonize CD200R and inhibit immune-complex stimulated IL-8 release from human CD200R-expressing U937 cells is also examined. For stimulation, human IgG1 isotype control antibody is coated at 10 µg/ml to a high-binding plate overnight. The next day, $4 \times 10^5$ CD200R-expressing U937 cells/well are incubated with different concentrations of Antibody IgG4PAA (the two leucine to alanine substitutions (SLL228PAA) are known to disrupt hydrophobic interactions with FcγRs to eliminate residual effector function) or Antibody I-4P for 1 hour on ice before added to the pre-coated plate for IC-stimulation followed by an incubated at 37° C. for 24 hours. The cells are spun down, the supernatant is removed, and the IL-8 concentration measured using MSD kit (Mesoscale Diagnostics) according to manufacturer's instructions. The IL-8 concentrations are converted to percent inhibition relative to isotype control. The IL-8 concentration are plotted versus the antibody concentration, and a 4 parameter logistic model is used to fit percent inhibition versus log concentration using R statistical software. According to procedures essentially as described above, the following data (shown in Table 4) were obtained.

TABLE 4

Concentration-dependent reduction in IL-8 production

| Antibody | IgG4PAA | | IgG4SP | |
|---|---|---|---|---|
| µg/ml | avg % IL-8 inhibition | SEM* | avg % IL-8 inhibition | SEM* |
| 0.01 | −3.2 | 6.0 | 15.4 | 3.7 |
| 0.03 | −5.0 | 5.6 | 35.8 | 3.6 |
| 0.1 | −10.4 | 10.1 | 44.0 | 3.0 |
| 0.3 | 15.0 | 5.3 | 80.0 | 2.8 |
| 1 | 16.9 | 3.9 | 73.8 | 1.8 |
| 3 | 35.5 | 4.1 | 82.0 | 2.6 |
| 10 | 45.4 | 1.7 | 87.1 | 1.4 |
| 30 | 53.5 | 3.2 | 86.4 | 1.5 |

*Standard error of the mean
These data demonstrate that IgG4PAA has weaker inhibitory activity ($IC_{50}$ = 1.45 µg/ml) compared to Antibody I-4P ($IC_{50}$ = 0.07 µg/ml).

EXAMPLE: FCγ RECEPTOR BINDING IS REQUIRED FOR AGONISM IN VIVO

Clustering Through Fcγ Receptor in the Lipid Raft can Increase the Inhibitory potency on inflammatory cells. In order to identify whether Fcγ Receptor interaction is beneficial for agonism through CD200R, two mouse CD200R antibodies are engineered; one to ablate any Fcγ Receptor binding (mIgG2aAA) and one to have functional Fcγ Receptor binding (mIgG2a). Both molecules are tested in two independent models of induced inflammatory disease in mice; contact dermatitis and CD40-induced colon inflammation model.

Contact dermatitis model: The ability of anti-human CD200R agonist antibodies to treat contact dermatitis may be determined by an in vivo mouse model performed essentially as described as follows (see e.g. Tolstrup et al., Anti-inflammatory effect of a retrovirus-derived immunosuppressive peptide in mouse models, BMC Immunology 2013, 14:51). Male 12 week-old C57Bl/6J mice are anesthetized, their abdomens are shaved, and 100 µL of 3% oxazalone in ethanol is applied to the shaved area. Seven days after sensitization, CD200R agonist antibody IgG2a or IgG2aAA is administered at 0.1, 1, or 10 mg/kg subcutaneously (SC), or an isotype control mIgG2a is administered at 10 mg/kg SC for comparison. Four hours after antibody administration, mice are anesthetized, baseline ear thickness is measured with calipers, and ears are challenged with 10 μL of 2% oxazalone in ethanol on each side of both ears. Twenty-four hours post-challenge, ear thickness is again measured. The hypersensitivity reaction is assessed by measuring the difference between ear thickness pre- and 24 hours post-challenges. Statistical differences from isotype control are determined using a 1-way ANOVA with Dunnett's post post test (GraphPad Prism).

CD40-induced colon inflammation model: The ability of anti-human CD200R agonist antibodies to treat CD40-induced colon inflammation model may be determined by an in vivo mouse model performed essentially as described as follows. Female 14 week-old RAG2N12 (B6.129S6-Rag2tm1Fwa N12; Taconic) mice are injected with 100 μg/mouse anti-CD40 antibody (BioXcel clone FGK4.5) to induce colon inflammation. One hour post-induction of disease, CD200R agonist antibody IgG2a, IgG2aAA, or isotype control antibody is administered subcutaneously at 0.1, 1, or 10 mg/kg. Animals are sacrificed six days later and colon inflammation is determined by measuring the length and the weight of the colon. The colon length-to-weight ratio is used to determine colon inflammation. Statistical differences from isotype control are determined using a 1-way ANOVA with Dunnett's post post test (GraphPad Prism).

Following procedures essentially as described above, the following data were obtained.

TABLE 5

Ear inflammation as measured in the contact dermatitis model by change in ear thickness (mm)
Ear thickness (mm)

|  | mIgG2a | mIgG2aAA |
|---|---|---|
| Isotype control | 0.200 ± 0.05 | 0.200 ± 0.05 |
| 10 mg/kg | 0.118 ± 0.03** | 0.160 ± 0.03* |
| 1.0 mg/kg | 0.113 ± 0.06** | 0.170 ± 0.04 |
| 0.1 mg/kg | 0.176 ± 0.05 | 0.178 ± 00.3 |

*$p < 0.05$;
**$p < 0.001$.
n = 5/group

TABLE 6

Colon inflammation as measured in the CD40-induced colon inflammation model by weight-to-length ratio (mg/cm)
Colon length to weight ratio (mg/cm)

|  | mIgG2a | mIgG2aAA |
|---|---|---|
| Isotype control | 37 ± 1.1 | 37 ± 1.1 |
| 10 mg/kg | 26 ± 0.8** | 33 ± 0.7 |
| 1.0 mg/kg | 29 ± 1.6* | 36 ± 1.9 |
| 0.1 mg/kg | 32 ± 2.6 | 36 (n = 1) | n = 5/group,
*$p < 0.05$;
**$p < 0.001$.

These data demonstrate that compared to isotype controls, the antibody with full effector function (mIgG2a) exhibited an immune suppressive function in both models. However, the Fcγ Receptor null variant (mIgG2aAA) was much less potent in the contact dermatitis model and had little to no effect in the colon inflammation model. The difference in activity was not due to depletion of CD200R-expressing cells, as the Fcγ Receptor-competent IgG2a antibody was demonstrated in an independent experiment not to deplete CD200R expressing cells in mice (data not shown).

These data demonstrate that Fcγ Receptor binding is required to provide optimal agonism to the CD200R to mediate an anti-inflammatory signal.

EXAMPLE: ANTIBODY I BINDING TO FCγ RECEPTORS

To determine if the antibody Fc affects the binding characteristics of Antibody I-4P to Fcγ receptors, the binding of Antibody I-4P, Antibody I-IgG1, and Antibody I-4PAA, to the human FcγRI, FcγRIIa, FcγRIIb, and FcγRIIIa receptor extracellular domains (ECDs) is measured by SPR at 25° C. Antibody I-IgG1 and Antibody I-4PAA have the same CDRs as Antibody I-4P. Antibody I-IgG1 has identical HCVR, LCVR, and LC as Antibody I-4P, but Antibody I-IgG1 has a HC whose amino acid sequence is given by SEQ ID NO: 11. Antibody I-4PAA differs from Antibody I-4P by having a SLL228PAA mutation in the HC.

Biacore® T100 instrument and Biacore® 3000 (GE Healthcare, Piscataway, N.J.), Biacore® reagents and Scrubber2 Biacore® Evaluation Software (Biologics 2008) are used for the SPR analysis of antibody binding. A CM5 chip (Biacore® P/N BR-1006-68) is prepared using the manufacturer's EDC/NHS amine coupling method (Biacore® P/N BR-1000-50). Briefly, the surfaces of all 4 FCs are activated by injecting a 1:1 mixture of EDC/NHS for 7 minutes at 10 μL/minute. Protein A (Calbiochem P/N 539202) is diluted to 100 μg/mL in 10 mM acetate, pH 4.5 buffer and immobilized for approximately 400 RU onto all 4 flow cells by 7 minute injection at a flow rate of 10 μL/minute. Un-reacted sites are blocked with a 7-minute injection of ethanolamine at 10 μL/minute. Injections of 2×10 μL of glycine pH 1.5 are used to remove any non-covalently associated protein.

The FcγR ECDs-FcγRI (CD64), FcγRIIA_131R, and FcγRIIA_131H (CD32a), FcγRIIIA_158V, FcγRIIIA_158F (CD16a), and FcγRIIb (CD32b; inhibitory receptor) (see e.g. Bruhns et al., Blood. 2009 Apr. 16; 113(16):3716-25) are produced from stable CHO cell expression according to methods well-known in the art and purified using IgG Sepharose and size exclusion chromatography.

For FcγRI binding, antibodies are diluted to 2.5 μg/mL in running buffer (1× HBS-EP+(Biacore® P/N BR-1006-69), and approximately 150 RU of each antibody is captured in flow cells 2 through 4 (RUcaptured). FC1 is the reference flow cell, therefore, no antibody is captured in FC1. FcγRI ECD is diluted to 200 nM in running buffer and then two-fold serially diluted in running buffer to 0.78 nM. Duplicate injections of each concentration are injected over all FCs at 40 μL/minute for 120 seconds followed by a 1200 second dissociation phase. Regeneration is performed by injecting 15 μL of 10 mM glycine pH 1.5 at 30 μL/minute over all FCs. Reference-subtracted data is collected as FC2-FC1, FC3-FC1, and FC4-FC1. The measurements are obtained at 25° C. The affinity ($K_D$) is calculated using either steady state equilibrium analysis with the Scrubber 2 Biacore® Evaluation Software or a "1:1 (Langmuir) binding" model in BIA Evaluation.

For FcγRIIa, FcγRIIb, and FcγRIIIa binding, antibodies are diluted to 5 μg/mL in running buffer, and approximately 500 RU of each variant is captured in flow cells 2 through 4 (RUcaptured). FC1 is the reference flow cell. Fcγ receptor ECDs are diluted to 10 μM in running buffer and then 2 fold serially diluted in running buffer to 39 nM. Duplicate injections of each concentration are injected over all FCs at 40 μL/minute for 60 seconds followed by a 120 second dissociation phase. Regeneration is performed by injecting 15 µL of 10 mM glycine pH 1.5 at 30 µL/min over all FCs. Reference-subtracted data is collected as FC2-FC1, FC3-FC1, and FC4-FC1. The measurements are obtained at 25° C. The affinity ($K_D$) is calculated using the steady state equilibrium analysis with the Scrubber 2 Biacore® Evaluation Software.

Following procedures essentially as described above, the following data as shown in Table 7 were obtained.

TABLE 7

In Vitro Binding Parameters of Antibody I-4P, Antibody I-IgG1, and Antibody I-4PAA to Human Fcγ Receptor ECDs Measured Using SPR at 25° C.

| Sample | Human Ligand | Average KD | Std Dev* |
|---|---|---|---|
| IgG1 Control Antibody | Fcγ RI | 56.1 pM | 2.2 |
| IgG4 PAA Control Antibody | Fcγ RI | 229.0 nM | 11.5 |
| Antibody I-IgG1 | Fcγ RI | 48.9 pM | 2.2 |
| Antibody I-4PAA | Fcγ RI | 273.3 nM | 12.6 |
| Antibody I-4P | Fcγ RI | 369.3 pM | 9.2 |
| IgG1 Control Antibody | Fcγ RIIA_131H | 0.5 µM | 0.0 |
| IgG4 PAA Control Antibody | Fcγ RIIA_131H | >10 µM | |
| Antibody I-IgG1 | Fcγ RIIA_131H | 0.5 µM | 0.0 |
| Antibody I-4PAA | Fcγ RIIA_131H | >10 µM | |
| Antibody I-4P | Fcγ RIIA_131H | 3.9 µM | 0.3 |
| IgG1 Control Antibody | Fcγ RIIA_131R | 0.6 µM | 0.0 |
| IgG4 PAA Control Antibody | Fcγ RIIA_131R | >10 µM | |
| Antibody I-IgG1 | Fcγ RIIA_131R | 0.6 µM | 0.0 |
| Antibody I-4PAA | Fcγ RIIA_131R | >10 µM | |
| Antibody I-4P | Fcγ RIIA_131R | 1.7 µM | 0.1 |
| IgG1 Control Antibody | Fcγ RIIb | 2.8 µM | 0.1 |
| IgG4 PAA Control Antibody | Fcγ RIIb | >10 µM | |
| Antibody I-IgG1 | Fcγ RIIb | 2.8 µM | 0.1 |
| Antibody I-4PAA | Fcγ RIIb | >10 µM | |
| Antibody I-4P | Fcγ RIIb | 2.2 µM | 0.1 |
| IgG1 Control Antibody | Fcγ RIIIA_158V | 0.2 µM | 0.0 |
| IgG4 PAA Control Antibody | Fcγ RIIIA_158V | 8.9 µM | 1.1 |
| Antibody I-IgG1 | Fcγ RIIIA_158V | 0.2 µM | 0.0 |
| Antibody I-4PAA | Fcγ RIIIA_158V | >10 µM | |
| Antibody I-4P | Fcγ RIIIA_158V | 4.3 µM | 0.4 |
| IgG1 Control Antibody | Fcγ RIIIA_158F | 1.0 µM | 0.1 |
| IgG4 PAA Control Antibody | Fcγ RIIIA_158F | >10 µM | |
| Antibody I-IgG1 | Fcγ RIIIA_158F | 0.9 µM | 0.1 |
| Antibody I-4PAA | Fcγ RIIIA_158F | >10 µM | |
| Antibody I-4P | Fcγ RIIIA_158F | >10 µM | |

Assay was performed three independent times.
*Standard deviation was not determined for measurements >10 µM.

Table 7 summarizes the affinity ($K_D$) of Antibody I-IgG1, Antibody I-4PAA, and Antibody I-4P to the human FcγRI, FcγRIIa, FcγRIIb, and FcγRIIIa receptor ECDs as measured by SPR. The binding characteristics of Antibody I-4P demonstrate binding to the Fcγ receptors with affinities that are substantially in between the binding affinities of IgG1 control/Antibody I-IgG1 and IgG4 PAA control/Antibody I-4PAA. For example, the data demonstrate that Antibody I-4P has reduced binding to FcγRIIIa receptor ECD compared to Antibody I-IgG1 (which can be attributed to cytokine release in the whole blood assay) but still has a higher binding affinity to FcγRI and FcγRIIb receptor ECDs compared to Antibody I-4PAA.

The binding characteristics demonstrated by Antibody I-4P to FcγRs are thought to contribute to enhanced in vivo efficacy without causing significant cytokine release.

EXAMPLE: IGG1 FC MUTANTS BINDING TO FCγ RECEPTORS

IgG1 antibodies are known to induce cytokine release. To determine the mechanism for IgG1-induced cytokine release, IgG1-Fc mutations are generated. These CD200R antibodies have different CDRs from Antibody I. The antibodies in Table 8 (IgG1, no mutations, P331S, P331S+S267G, A330S+P331S+S267G, A330S+S267G, K322A, K322A+S267G, and N325S+L328F+S267G) have identical CDRs with one another. The S267G antibody has different CDRs from the other antibody mutants and Antibody I-4P.

An S267G mutation is generated to reduce FcγRIII binding (EU numbering: see, e.g., Kabat et al., "Sequences of Proteins of Immunological Interest," National Institutes of Health, Bethesda, Md. (1991); and Shields R L et al., High resolution mapping of the binding site on human IgG1 for Fc gamma RI, Fc gamma RII, Fc gamma RIII, and FcRn and design of IgG1 variants with improved binding to Fc gamma R. 2001 J. Biol. Chem. 276, 6591-6604).

The S267G mutation is also combined with mutations that reduce C1q binding without significantly impacting FcγR-binding (K322A, A330S, and P331S; see e.g. Oganesyan V et al., 2008 Structural characterization of a human Fc fragment engineered for lack of effector functions. Acta Crystallogr. D Biol. Chrystallogr. 64, 700-704; Idusogie, E et al., 2000 Mapping of the C1q Binding Site on Rituxan, a Chimeric Antibody with a Human IgG1 Fc. J. of Immunology, 164(8) 4178-4184; and Tao M. H. and Morrison M. L. 1993 Structural features of human immunoglobulin G that determine isotype-specific differences in complement activation. J. of Exp. Med., 178(2), 661-667). Additional mutations that reduce FcγRIII and C1q binding while modulating binding to FcγRIIA and FcγRIIB are also generated (N325S+L328F; see e.g. Shang L et al., 2014 Selective antibody intervention of Toll-like receptor 4 activation through FcγR tethering. J. Biol. Chem. 289, 15309-18; Monnet E et al., 2017 Evidence of NI-0101 pharmacological activity, an anti-TLR4 antibody, in a randomized phase I dose escalation study in healthy volunteers receiving LPS. Clin Pharmacol Ther. 2017 101, 200-208). Fcγ receptor binding is determined by Biacore®, and IFNγ is determined by a multiplex assay based on the Mesoscale platform, both as described herein. C1q binding is determined by ELISA. For the ELISA, a 96 well microplate is coated with 100 µL/well of each antibody diluted in DPBS (Dulbecco's HyClone) with a concentration range of 10 µg/mL to 0.19 µg/mL. Testing is performed in duplicate wells. The plate is sealed and incubated overnight at 4° C. The coating reagent is removed from each well, and 200 µL/well of casein blocking reagent (Thermo) is added. The plate is sealed and incubated for 2 hours at room temperature (RT). Each well is washed 3 times with Wash Buffer (1× TBE with 0.05% Tween 20). 100 µL/well of Human C1q (MS Biomedical) at 10 µg/mL diluted in casein blocking reagent is added and incubated for 3 hours at RT. The plate is then washed three times with wash buffer before 100 µL/well of a 1:800 times dilution of Sheep anti-human C1q-HRP (Abcam #ab46191) in casein blocker is added and incubated for 1 hour at RT. The plate is washed 6 times with wash buffer, and 100 µL/well of TMB Substrate (Pierce) is added to each well and incubated for 7 minutes. 100 µL of 1 N HCl is added to each well to stop the reaction. Optical density is immediately measured using a colorimetric microplate reader set to 450 nm.

Following procedures essentially as described above, the following data were obtained (N=1; Table 8).

TABLE 8

FcγR and C1q binding and whole blood cytokine release measurements with IgG1 mutants.

| Mutation | FcγRI, pM | FcγRIIA_131H, μM | FcγRIIA_131R, μM | FcγRIIb, μM | FcγRIIIA_158V, μM | FcγRIIIA_158F, μM | C1q Elisa | Whole Blood IFNγ Release[a] |
|---|---|---|---|---|---|---|---|---|
| Hu IgG1 | 55.2 | 0.71 | 1.03 | 4.2 | 0.28 | 2.59 | ++ | ND |
| IgG1, no mutations | 46.4 | 0.69 | 1.04 | 4.23 | 0.27 | 2.12 | +++ | Yes |
| P331S | 54.3 | 1.15 | 1.14 | 4.64 | 0.45 | 3.11 | + | Yes |
| P331S + S267G | 142.4 | 5.2 | 0.77 | 4.38 | 2.08 | >10 | − | No |
| A330S + P331S + S267G | 511.4 | 5.1 | 0.78 | 4.3 | 2.48 | 9.8 | − | No |
| A330S + S267G | 167.7 | 3.31 | 0.82 | 4.99 | 1.66 | 10.83 | − | No |
| K322A | 30.5 | 0.98 | 0.82 | 3.41 | 0.28 | 2.58 | − | Yes |
| K322A + S267G | 70.5 | 5.02 | 0.66 | 4.43 | 1.65 | 9.99 | − | No |
| N325S + L328F | 68.7 | 2.64 | 0.06 | 0.275 | 7.35 | >10 | − | No |
| S267G | 130.7 | 3.13 | 0.53 | 3.41 | 0.73 | 4.5 | | Yes |
| Human IgG4P control antibody | 384.7 | 5.12 | 2.89 | 3.31 | 5.47 | >10 | − | No |

[a] Any cytokine release significantly above baseline levels within whole blood is recorded as 'Yes', however, the exact levels over baseline may vary.

These data demonstrate that combining mutations that reduce C1q binding and alter FcγR binding leads to a lack of IFNγ release over baseline, which suggests a more desirable safety profile when administered to patients. For example, reducing C1q binding and reducing binding to FCγRIII (or FCγRI) results in a lack of IFNγ release over baseline.

EXAMPLE: IN VITRO CYTOKINE RELEASE

Clinical toxicity, including cytokine release syndrome (CRS), has been associated with the administration of antibodies. CRS, one of the most severe adverse events associated with monoclonal antibodies, is characterized by high levels of immune cell activation and rapid systemic release of pro-inflammatory cytokines and can potentially be fatal. Importantly, preclinical models do not adequately predict the potential risk for CRS. Consequently, an in vitro cytokine release assay using human blood cells is developed to mitigate potential risks of CRS after antibody administration. Antibody, in particular IgG1 antibody, binding to Fcγ receptors can cause unwanted cytokine release.

To determine whether Antibody I-4P or Antibody I-IgG1 induce cytokine release from unstimulated human whole blood, an in vitro cytokine release study is performed. Freshly collected whole blood from six healthy humans are incubated with 100 μg/ml of Antibody I-4P, Antibody I-IgG1, or control IgG1 antibody for 24 hours. The positive control is a homolog of Campath-1H (anti-CD52) IgG1 antibody known to cause cytokine release syndrome in clinic. The negative control is an hIgG1 antibody that does not cause cytokine release. Using a commercially available multiplex assay based on the Mesoscale platform, ten cytokines including IFN-γ, IL-2, IL-6, IL-13, IL-8, IL-12p70, IL-10, and TNF-α are measured in cell culture supernatants.

Following procedures essentially as described above, the following data were obtained. As shown in Table 9, incubation of whole blood with 10 μg/ml positive control antibody resulted in robust cytokine production for 9 of the 10 cytokines analyzed in most donors. Incubation of whole blood with Antibody I-IgG1 induced a significant release of IFN-γ. Incubation of whole blood with 100 μg/ml Antibody I-4P or 100 μg/ml negative control IgG1 did not result in significant levels of any of the evaluated cytokines.

TABLE 9

| | Fold change relative to baseline (PBS control sample); MEDIAN ± SEM | | | |
|---|---|---|---|---|
| Cytokine | Antibody I-IgG1 | Antibody I-4P | Negative control | Positive control |
| IFN-γ | 10 ± 19 | 0.9 ± 0.08 | 0.8 ± 0.06 | 612 ± 431 |
| IL-1β | 1.8 ± 3 | 1.19 ± 2 | 1.04 ± 1.4 | 3 ± 5 |
| IL-2 | 0.36 ± 0.14 | 1.7 ± 0.133 | 1.9 ± 0.86 | 1.33 ± 1.3 |
| IL-4 | 0.96 ± 1.4 | 1.08 ± 0.42 | 0.83 ± 0.73 | 10 ± 24 |
| IL-6 | 1.25 ± 1.8 | 1.17 ± 0.17 | 1.03 ± 0.13 | 15 ± 18 |
| IL-8 | 1.1 ± 0.58 | 1.2 ± 0.08 | 1.25 ± 0.24 | 8.8 ± 5 |
| IL-10 | 0.88 ± 0.11 | 1.25 ± 0.15 | 1.26 ± 0.3 | 3.9 ± 2.6 |
| IL-12p70 | 0.97 ± 0.37 | 0.63 ± 0.19 | 0.49 ± 0.5 | 7 ± 11 |
| IL-13 | 1.18 ± 0.27 | 1.18 ± 0.12 | 1.1 ± 0.24 | 5.5 ± 1.89 |
| TNF-α | 1.37 ± 0.4 | 1.1 ± 0.05 | 0.96 ± 0.07 | 20 ± 17 |

These data demonstrate that Antibody I-4P does not cause significant cytokine release, and suggest a low risk of cytokine release in the clinic following administration of Antibody I-4P.

EXAMPLE: ANTIBODY I DOES NOT BLOCK BINDING OF CD200 TO CD200R

Both CD200 and CD200R are cell-expressed molecules and contain two Ig-like domains. They interact through their NH2 terminal domains compatible with immunological synapse-like interactions occurring between myeloid cells and other CD200-expressing cells. To determine if Antibody I-4P binds CD200R in the presence of ligand, co-binding experiments on HEL92.7.1 cells, a human erythroblastoma cell line which expresses CD200R, are performed by flow cytometry. For the study, $2^{e5}$ cells are incubated (pre-treated) with 300 nM of CD200Fc (RD Systems; fusion protein of immunoglobulin 1 Fc region with CD200), Antibody I-4P, isotype control antibody, or PBS for one hour at room temperature. Cells are washed 3 times and incubated with Fc block (Miltenyi Biotec) for 20 minutes at room temperature. The cells are stained with various concentrations of AF647-labeled Antibody I-4P for one hour at room temperature and cells are then washed and suspended in FACS buffer for analysis by flow cytometry.

The median fluorescence intensity (MFI) is determined for each concentration of AF647-labeled Antibody I-4P, and the MFI indicates the amount of binding in the presence of ligand. Following procedures essentially as described above, the data in Table 10 were obtained.

TABLE 10

Antibody binding in the presence of CD200.

| Stain Antibody I-4P-AF647 (ug/mL) | No Pre-treatment No Pre-treatment (MFI) | Pre-Treatment Isotype Control (MFI) | Pre-Treatment Antibody I-4P (MFI) | Pre-Treatment CD200-Fc (MFI) |
|---|---|---|---|---|
| 0 | 49.1 | 49.1 | 49.1 | 49.1 |
| 0.4 | 416 | 399 | 70.4 | 230 |
| 0.8 | 694 | 664 | 76.3 | 370 |
| 1.6 | 1184 | 1154 | 96.9 | 630 |
| 3.125 | 1979 | 1914 | 133 | 1068 |
| 6.25 | 3097 | 2987 | 200 | 1728 |
| 12.5 | 4216 | 4105 | 319 | 2641 |
| 25 | 5137 | 4916 | 496 | 3421 |
| 50 | 5651 | 5515 | 745 | 3957 |

These data demonstrate that Antibody I-4P does not block CD200 ligand from binding human CD200R (human CD200-Fc data compared to isotype control and no pre-treatment data). The Antibody I-4P pre-treatment data serve as a control and demonstrate reduced labeled Antibody I-4P binding following pre-treatment with Antibody I-4P.

The epitope for Antibody I-4P was determined to be close to the cell membrane on domain 2 of CD200R (data not shown).

EXAMPLE: ANTIBODY I-4P INHIBITS CONTACT HYPERSENSITIVITY IN HUMANIZED MICE

To demonstrate the anti-inflammatory effects of Antibody I-4P, female huNOG-EXL mice (NOD.Cg-Prkdc$^{scid}$ Il2rg$^{tm1Sug}$ Tg(SV40/HTLV-IL3,CSF2)10-7Jic/JicTac) are purchased from Taconic Biosciences at 20 weeks of age and allowed to acclimate for more than 1 week. Mice are housed four mice per cage at 22° C. under a 12 h light:dark cycle and allowed food and water ad libitum. On day 0, mice are anesthetized with 5% isoflurane, their abdomens are shaved, and 100 µL of 3% oxazalone in ethanol is applied to the shaved area. Five days after sensitization, Antibody I-4P is administered at 1 or 10 mg/kg subcutaneously (SC); IgG4P isotype control is administered at 10 mg/kg SC for comparison. Four hours after antibody administration, mice are anesthetized with 5% isoflurane, ear thickness is measured with calipers, and ears are challenged with 10 µL of 2% oxazalone in ethanol on each side of both ears. The challenge procedure is repeated on days 10 and 14. The hypersensitivity reaction is assessed by measuring the difference between ear thickness pre- and 24 hours post-challenges.

Statistics: Inflammation is determined by measuring the differences in ear thickness from pre- to 24 hours post challenges for each challenge. Percent inhibition is calculated from the mean ear thickness of the isotype controls set to 0% inhibition. Statistical differences from isotype control are determined using a 1-way or 2-way ANOVA with Dunnett's test where appropriate (GraphPad Prism).

Following procedures essentially as described above, the following data were obtained. As shown in Table below, a single treatment with Antibody I-4P at 1 or 10 mg/kg SC 4 hours prior to the first challenge significantly ameliorated the inflammatory response after the 3rd challenge compared to isotype-treated mice.

TABLE 11

| Treatment | Delta ear thickness (mm) ± SEM | % inhibition of isotype | p-value |
|---|---|---|---|
| Isotype control | 0.108 ± 0.005 | N/A | |
| Antibody I-4P 10 mg/kg | 0.056 ± 0.008 | 47.9 ± 7.8 | 0.0001 |
| Antibody I-4P 1 mg/kg | 0.064 ± 0.007 | 41.4 ± 6.4 | 0.0001 |

SEQUENCES

HCDR1 of Antibody I-4P and Antibody I-IgG1 (SEQ ID NO: 1)
KASGFSFSSGYYMA

HCDR2 of Antibody I-4P and Antibody I-IgG1 (SEQ ID NO: 2)
LIGVGSGSLWYAQKFQG

HCDR3 of Antibody I-4P and Antibody I-IgG1 (SEQ ID NO: 3)
ARHFALSDPFNL

LCDR1 of Antibody I-4P and Antibody I-IgG1 (SEQ ID NO: 4)
QASESIDSYLL

LCDR2 of Antibody I-4P and Antibody I-IgG1 (SEQ ID NO: 5)
KQASTLAS

LCDR3 of Antibody I-4P and Antibody I-IgG1 (SEQ ID NO: 6)
QNYYDISSND

| SEQUENCES |
| --- |

Antibody HCVR of Antibody I-4P and Antibody I-IgG1 (SEQ ID NO: 7)
XVQLVQSGAEVKKPGASVKVSCKASGFSFSSGYYMAWVRQAPGQGLEWMGLI
GVGSGSLWYAQKFQGRVTMTRDTSTSTVYMELSSLRSEDTAVYYCARHFALSDP
FNLWGQGTLVTVSS
wherein Xaa at position 1 is either glutamine or pyroglutamic acid Antibody LCVR of Antibody I-4P and Antibody I-IgG1 (SEQ ID NO: 8)
EIVLTQSPDFQSVTPKEKVTITCQASESIDSYLLWYQQKPDQSPKLLIKQASTLASG
VPSRFSGSGSGTDFTLTINSLEAEDAATYYCQNYYDISSNDFGGGTKVEIK Antibody Heavy Chain of Antibody I-4P (SEQ ID NO: 9)
XVQLVQSGAEVKKPGASVKVSCKASGFSFSSGYYMAWVRQAPGQGLEWMGLI
GVGSGSLWYAQKFQGRVTMTRDTSTSTVYMELSSLRSEDTAVYYCARHFALSDP
FNLWGQGTLVTVSSASTKGPSVFPLAPCSRSTSESTAALGCLVKDYFPEPVTVSW
NSGALTSGVHTFPAVLQSSGLYSLSSVVTVPSSSLGTKTYTCNVDHKPSNTKVDK
RVESKYGPPCPPCPAPEFLGGPSVFLFPPKPKDTLMISRTPEVTCVVVDVSQEDPE
VQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHN
HYTQKSLSLSLX
wherein Xaa at position 1 is either glutamine or pyroglutamic acid; and Xaa at position
446 is either glycine or absent.

Antibody Light Chain of Antibody I-4P and Antibody I-IgG1 (SEQ ID NO: 10)
EIVLTQSPDFQSVTPKEKVTITCQASESIDSYLLWYQQKPDQSPKLLIKQASTLASG
VPSRFSGSGSGTDFTLTINSLEAEDAATYYCQNYYDISSNDFGGGTKVEIKRTVAA
PSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC Antibody Heavy Chain of Antibody I-IgG1 (SEQ ID NO: 11)
XVQLVQSGAEVKKPGASVKVSCKASGFSFSSGYYMAWVRQAPGQGLEWMGLI
GVGSGSLWYAQKFQGRVTMTRDTSTSTVYMELSSLRSEDTAVYYCARHFALSDP
FNLWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHE
ALHNHYTQKSLSLSPGX
wherein Xaa at position 1 is either glutamine or pyroglutamic acid; and Xaa at position
450 is either lysine or absent.

DNA Encoding Heavy Chain of Antibody I-4P (SEQ ID NO: 12)
caggtgcagctggtgcagtctggggctgaggtgaagaagcctcagtgaaggtttcctgcaaggcatctggattctcc
ttcagtagcggctactacatggcatgggtgcggcaggcccctggacaagggcttgagtggatgggactgattggtgttggtagt
ggtagcctatggtacgcgcagaagttccaaggccgggtcaccatgaccagggacacgtccacgagcacagtctatatggagct
gagcagcctgagatctgaggacacggccgtgtattactgtgcgagacattttgctctgtctgatccctttaacttgtggggccagg
gcacactcgtcaccgtctcctcagctagcaccaagggcccatccgtcttcccctggcacctgtccaggagcacctccgaga
gcacagccgccctgggctgcctggtcaaggactacttccccgaaccggtgacggtgtcgtggaactcaggcgccctgaccag
cggcgtgcacacttcccggctgtcctacagtcctcaggactctactccctcagcagcgtggtgaccgtgccctccagcagcttg
ggcacgaagacctacacctgcaacgtagatcacaagcccagcaacaccaaggtggacaagagagttgagtccaaatatggtc
ccccatgcccaccctgcccagcacctgagttcctggggggaccatcagtcttcctgttcccccccaaaacccaaggacactctcat
gatctcccggacccctgaggtcacgtgcgtggtggtggacgtgagccaggaagaccccgaggtccagttcaactggtacgtg
atggcgtggaggtgcataatgccaagacaaagccgcgggaggagcagttcaacagcacgtaccgtgtggtcagcgtcctcac
cgtcctgcaccaggactggctgaacggcaaggagtacaagtgcaaggtctccaacaaaggcctcccgtcctccatcgagaaaa
ccatctccaaagccaaagggcagccccgagagccacaggtgtaccacctgcccccatcccaggaggagatgaccaagaacc
aggtcagcctgacctgcctggtcaaaggcttctaccccagcgacatcgccgtggagtgggaaagcaatgggcagccggagaa
caactacaagaccacgcctcccgtgctggactccgacggctccttcttcctctacagcaggctaaccgtggacaagagcaggtg
gcaggaggggaatgtcttctcatgctccgtgatgcatgaggctctgcacaaccactacacacagaagagcctctccctgtctctg
ggt DNA Encoding Light Chain of Antibody I-4P and Antibody I-IgG1 (SEQ ID NO: 13)
gaaattgtgctgactcagtctccagactttcagtctgtgactccaaaggagaaagtcaccatcacctgccaggccagtgagtcgat
tgatagctatttactgtggtaccagcagaaaccagatcagtctccaaagctcctcatcaagcaggcatccactctggcatctgggg
tccccctcgaggttcagtggcagtggatctgggacagatttcaccctcaccatcaatagcctggaagctgaagatgctgcaacgtat
tactgtcaaaactattatgatattagtagtaatgatttcggcggagggaccaaggtggagatcaaaacgaccgtggctgcaccatc
tgtcttcatcttcccgccatctgatgagcagttgaaatctggaactgcctctgttgtgtgcctgctgaataacttctatcccagagagg
ccaaagtacagtggaaggtggataacgccctccaatcgggtaactcccaggagagtgtcacagagcaggacagcaaggaca
gcacctacagcctcagcagcaccctgacgctgagcaaagcagactacgagaaacacaaagtctacgcctgcgaagtcaccca
tcagggcctgagctcgcccgtcacaaagagcttcaacaggggagagtgc DNA Encoding Heavy Chain of Antibody I-IgG1 (SEQ ID NO: 14)
caggtgcagctggtgcagtctggggctgaggtgaagaagcctggggcctcagtgaaggtttcctgcaaggcatctggattctcc
ttcagtagcggctactacatggcatgggtgcggcaggcccctggacaagggcttgagtggatgggactgattggtgttggtagt
ggtagcctatggtacgcgcagaagttccaaggccgggtcaccatgaccagggacacgtccacgagcacagtctatatggagct
gagcagcctgagatctgaggacacggccgtgtattactgtgcgagacattttgctctgtctgatccctttaacttgtggggccagg

SEQUENCES

```
gcacactcgtcaccgtctcctcagctagcaccaagggcccatcggtcttccccctggcaccctcctccaagagcacctctgggg
gcacagcggccctgggctgcctggtcaaggactacttccccgaaccggtgacggtgtcgtggaactcaggcgccctgaccag
cggcgtgcacaccttcccggctgtcctacagtcctcaggactctactccctcagcagcgtggtgaccgtgccctccagcagcttg
ggcacccagacctacatctgcaacgtgaatcacaagcccagcaacaccaaggtggacaagaaagttgagcccaaatcttgtga
caaaactcacacatgcccaccgtgcccagcacctgaactcctggggggaccgtcagtcttcctcttccccccaaaacccaagga
caccctcatgatctcccggacccctgaggtcacatgcgtggtggtggacgtgagccacgaagaccctgaggtcaagttcaactg
gtacgtggacggcgtggaggtgcataatgccaagacaaagccgcgggaggagcagtacaacagcacgtaccgtgtggtcag
cgtcctcaccgtcctgcaccaggactggctgaatggcaaggagtacaagtgcaaggtctccaacaaagcccctcccagcccca
tcgagaaaaccatctccaaagccaaagggcagccccgagaaccacaggtgtacaccctgcccccatcccgggatgagctgac
caagaaccaggtcagcctgacctgcctggtcaaaggcttctatcccagcgacatcgccgtggagtgggagagcaatgggcag
ccggagaacaactacaagaccacgcctcccgtgctggactccgacggctccttcttcctctacagcaagctcaccgtggacaag
agcaggtggcagcaggggaacgtcttctcatgctccgtgatgcatgaggctctgcacaaccactacacgcagaagagcctctcc
ctgtctccgggtaag
```

Human CD200R (SEQ ID NO: 15)
MLCPWRTANLGLLLILTIFLVAEAEGAAQPNNSLMLQTSKENHALASSSLCMDE
KQITQNYSKVLAEVNTSWPVKMATNAVLCCPPIALRNLIIITWEIILRGQPSCTKA
YRKETNETKETNCTDERITWVSRPDQNSDLQIRPVAITHDGYYRCIMVTPDGNFH
RGYHLQVLVTPELTLFQNRNRTAVCKAVAGKPAAQISWIPEGDCATKQEYWSN
GTVTVKSTCHWEVHNVSTVTCHVSHLTGNKSLYIELLPVPGAKKSAKLYIPYIILT
IIILTIVGFIWLLKVNGCRKYKLNKTESTPVVEEDEMQPYASYTEKNNPLYDTTNK
VKASQALQSEVDTDLHTL Cynomolgus monkey CD200R (SEQ ID NO: 16)
MLCPWRTANLGLLLILAVFLVAEAEGAAQSNNSLMLQTSKENHTLASNSLCMDE
KQITQNHSKVLAEVNISWPVQMARNAVLCCPPIEFRNLIVITWEIILRGQPSCTKT
YRKDTNETKETNCTDERITWVSTPDQNSDLQIHPVAITHDGYYRCIMATPDGNFH
RGYHLQVLVTPEVTLFESRNRTAVCKAVAGKPAAQISWIPAGDCAPTEQEYWGN
GTVTVKSTCHWEGHNVSTVTCHVSHLTGNKSLYIELLPVPGAKKSAKLYMPYVI
LTIIILTIVGFIWLLKISGCRKYNLNKTESTSVVEEDEMQPYASYTEKNNPLYDTTN
KVKASQALQSEVGTDLHTL Cynomolgus monkey CD200RLa (SEQ ID NO: 17)
MHTLGKMSASRLLISIIIMVSASSSSCMDGKQMTQNYSKMSAEGNISQPVLMDTN
AMLCCPPIEFRNLIVIVWEIIRGQPSCTKAYRKETNETKETNCTDERITWVSTPDQ
NSDLQIHPVAITHDGYYRCIMATPDGNEHRGYHLQVLVTPEVTLFQSRNRTAVCK
AVAGKPAAQISWIPAGDCAPTEHEYWGNGTVTVESMCHWGDHNASTMTCHVS
HTLGNKSLYIKLNSGLRTSGSPALDLLIILYVKLSLFVVILVTTGFVFFQRINYVRK
SL

We claim:

1. An antibody comprising a heavy chain variable region (HCVR) and a light chain variable region (LCVR), wherein the HCVR comprises a HCDR1, HCDR2, and HCDR3, and the LCVR comprises a LCDR1, LCDR2, and LCDR3, wherein the amino acid sequence of the HCDR1 is SEQ ID NO: 1, the amino acid sequence of the HCDR2 is SEQ ID NO: 2, and the amino acid sequence of the HCDR3 is SEQ ID NO: 3, the amino acid sequence of the LCDR1 is SEQ ID NO: 4, the amino acid sequence of the LCDR2 is SEQ ID NO: 5, and the amino acid sequence of the LCDR3 is SEQ ID NO: 6, and wherein the antibody binds human CD200R.

2. The antibody of claim 1, comprising a HCVR and a LCVR, wherein the amino acid sequence of the HCVR is SEQ ID NO: 7 and the amino acid sequence of the LCVR is SEQ ID NO: 8.

3. The antibody of claim 2, wherein Xaa at position 1 of SEQ ID NO: 7 is glutamine.

4. The antibody of claim 2, wherein Xaa at position 1 of SEQ ID NO: 7 is pyroglutamic acid.

5. The antibody of claim 2, comprising a heavy chain (HC) and a light chain (LC), wherein the amino acid sequence of the HC is SEQ ID NO: 9 and the amino acid sequence of the LC is SEQ ID NO: 10.

6. The antibody of claim 5, wherein Xaa at position 1 of SEQ ID NO: 9 is glutamine.

7. The antibody of claim 5, wherein Xaa at position 446 of SEQ ID NO: 9 is glycine.

8. The antibody of claim 5, wherein Xaa at position 1 of SEQ ID NO: 9 is glutamine and Xaa at position 446 of SEQ ID NO: 9 is glycine.

9. The antibody of claim 5, wherein Xaa at position 1 of SEQ ID NO: 9 is glutamine and Xaa at position 446 of SEQ ID NO: 9 is absent.

10. The antibody of claim 5, wherein Xaa at position 1 of SEQ ID NO: 9 is pyroglutamic acid and Xaa at position 446 of SEQ ID NO: 9 is absent.

11. A pharmaceutical composition comprising i) an antibody comprising a heavy chain variable region (HCVR) and a light chain variable region (LCVR), wherein the HCVR comprises a HCDR1, HCDR2, and HCDR3, and the LCVR comprises a LCDR1, LCDR2, and LCDR3, wherein the amino acid sequence of the HCDR1 is SEQ ID NO: 1, the amino acid sequence of the HCDR2 is SEQ ID NO: 2, and the amino acid sequence of the HCDR3 is SEQ ID NO: 3, the amino acid sequence of the LCDR1 is SEQ ID NO: 4, the amino acid sequence of the LCDR2 is SEQ ID NO: 5, and the amino acid sequence of the LCDR3 is SEQ ID NO: 6, and ii) one or more pharmaceutically acceptable carriers, diluents, or excipients.

12. The pharmaceutical composition of claim 11 wherein the antibody comprises a heavy chain (HC) and a light chain (LC), wherein the amino acid sequence of the HC is SEQ ID NO: 9 and the amino acid sequence of the LC is SEQ ID NO: 10.

13. The pharmaceutical composition of claim 12 wherein Xaa at position 1 of SEQ ID NO: 9 is glutamine and Xaa at position 446 of SEQ ID NO: 9 is absent.

14. The pharmaceutical composition of claim 12, wherein Xaa at position 1 of SEQ ID NO: 9 is pyroglutamic acid and Xaa at position 446 of SEQ ID NO: 9 is absent.

* * * * *

UNITED STATES PATENT AND TRADEMARK OFFICE
CERTIFICATE OF CORRECTION

| | |
|---|---|
| PATENT NO. | : 11,319,370 B2 |
| APPLICATION NO. | : 16/567256 |
| DATED | : May 3, 2022 |
| INVENTOR(S) | : Stephen J. Demarest et al. |

It is certified that error appears in the above-identified patent and that said Letters Patent is hereby corrected as shown below:

On the Title Page

Page 2, Line 1 (Residence of 6th inventor), Column 1, item 72 (Inventors): Delete "San Diego," and insert -- Burlingame, --.

Signed and Sealed this
Sixth Day of September, 2022

Katherine Kelly Vidal
*Director of the United States Patent and Trademark Office*

SEQUENCE LISTING

<160> NUMBER OF SEQ ID NOS: 17

<210> SEQ ID NO 1
<211> LENGTH: 14
<212> TYPE: PRT
<213> ORGANISM: Artificial Sequence
<220> FEATURE:
<223> OTHER INFORMATION: Synthetic Construct

<400> SEQUENCE: 1

Lys Ala Ser Gly Phe Ser Phe Ser Ser Gly Tyr Tyr Met Ala
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Leu Ile Gly Val Gly Ser Gly Ser Leu Trp Tyr Ala Gln Lys Phe Gln
1               5                   10                  15

Gly

<210> SEQ ID NO 3

```
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Ala Arg His Phe Ala Leu Ser Asp Pro Phe Asn Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Gln Ala Ser Glu Ser Ile Asp Ser Tyr Leu Leu
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Lys Gln Ala Ser Thr Leu Ala Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Gln Asn Tyr Tyr Asp Ile Ser Ser Asn Asp
1               5                   10

<210> SEQ ID NO 7
<211> LENGTH: 120
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is either glutamine or
      pyroglutamic acid

<400> SEQUENCE: 7

Xaa Val Gln Leu Val Gln Ser Gly Ala Glu Val Lys Lys Pro Gly Ala
1               5                   10                  15

Ser Val Lys Val Ser Cys Lys Ala Ser Gly Phe Ser Phe Ser Ser Gly
            20                  25                  30

Tyr Tyr Met Ala Trp Val Arg Gln Ala Pro Gly Gln Gly Leu Glu Trp
        35                  40                  45

Met Gly Leu Ile Gly Val Gly Ser Gly Ser Leu Trp Tyr Ala Gln Lys
    50                  55                  60

Phe Gln Gly Arg Val Thr Met Thr Arg Asp Thr Ser Thr Ser Thr Val
65                  70                  75                  80
```

Tyr Met Glu Leu Ser Ser Leu Arg Ser Glu Asp Thr Ala Val Tyr Tyr
                85                  90                  95

Cys Ala Arg His Phe Ala Leu Ser Asp Pro Phe Asn Leu Trp Gly Gln
            100                 105                 110

Gly Thr Leu Val Thr Val Ser Ser
        115                 120

<210> SEQ ID NO 8
<211> LENGTH: 108
<212> TYPE: PRT
<213> ORGANISM: Artificial Sequence
<220> FEATURE:
<223> OTHER INFORMATION: Synthetic Construct

<400> SEQUENCE: 8

Glu Ile Val Leu Thr Gln Ser Pro Asp Phe Gln Ser Val Thr Pro Lys
1               5                   10                  15

Glu Lys Val Thr Ile Thr Cys Gln Ala Ser Glu Ser Ile Asp Ser Tyr
            20                  25                  30

Leu Leu Trp Tyr Gln Gln Lys Pro Asp Gln Ser Pro Lys Leu Leu Ile
        35                  40                  45

Lys Gln Ala Ser Thr Leu Ala Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Tyr Tyr Asp Ile Ser Ser
                85                  90                  95

Asn Asp Phe Gly Gly Gly Thr Lys Val Glu Ile Lys
            100                 105

<210> SEQ ID NO 9
<211> LENGTH: 446
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is either glutamine or
      pyroglutamic acid
<220> FEATURE:
<221> NAME/KEY: MISC_FEATURE
<222> LOCATION: (446)..(446)
<223> OTHER INFORMATION: Xaa at position 446 is either glycine or absent

<400> SEQUENCE: 9

Xaa Val Gln Leu Val Gln Ser Gly Ala Glu Val Lys Lys Pro Gly Ala
1               5                   10                  15

Ser Val Lys Val Ser Cys Lys Ala Ser Gly Phe Ser Phe Ser Ser Gly
            20                  25                  30

Tyr Tyr Met Ala Trp Val Arg Gln Ala Pro Gly Gln Gly Leu Glu Trp
        35                  40                  45

Met Gly Leu Ile Gly Val Gly Ser Gly Ser Leu Trp Tyr Ala Gln Lys
    50                  55                  60

Phe Gln Gly Arg Val Thr Met Thr Arg Asp Thr Ser Thr Ser Thr Val
65                  70                  75                  80

Tyr Met Glu Leu Ser Ser Leu Arg Ser Glu Asp Thr Ala Val Tyr Tyr
                85                  90                  95

Cys Ala Arg His Phe Ala Leu Ser Asp Pro Phe Asn Leu Trp Gly Gln

```
            100                 105                 110
Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Xaa
        435                 440                 445

<210> SEQ ID NO 10
<211> LENGTH: 215
<212> TYPE: PRT
<213> ORGANISM: Artificial Sequence
<220> FEATURE:
<223> OTHER INFORMATION: Synthetic Construct

<400> SEQUENCE: 10

Glu Ile Val Leu Thr Gln Ser Pro Asp Phe Gln Ser Val Thr Pro Lys
1               5                   10                  15

Glu Lys Val Thr Ile Thr Cys Gln Ala Ser Glu Ser Ile Asp Ser Tyr
```

```
                 20                  25                  30
Leu Leu Trp Tyr Gln Gln Lys Pro Asp Gln Ser Pro Lys Leu Leu Ile
             35                  40                  45

Lys Gln Ala Ser Thr Leu Ala Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Asn Tyr Tyr Asp Ile Ser Ser
                 85                  90                  95

Asn Asp Phe Gly Gly Gly Thr Lys Val Glu Ile Lys Arg Thr Val Ala
             100                 105                 110

Ala Pro Ser Val Phe Ile Phe Pro Pro Ser Asp Glu Gln Leu Lys Ser
             115                 120                 125

Gly Thr Ala Ser Val Val Cys Leu Leu Asn Asn Phe Tyr Pro Arg Glu
             130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 11
<211> LENGTH: 450
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is either glutamine or
      pyroglutamic acid
<220> FEATURE:
<221> NAME/KEY: MISC_FEATURE
<222> LOCATION: (450)..(450)
<223> OTHER INFORMATION: Xaa at position 450 is either lysine or absent

<400> SEQUENCE: 11

Xaa Val Gln Leu Val Gln Ser Gly Ala Glu Val Lys Lys Pro Gly Ala
 1               5                  10                  15

Ser Val Lys Val Ser Cys Lys Ala Ser Gly Phe Ser Phe Ser Ser Gly
             20                  25                  30

Tyr Tyr Met Ala Trp Val Arg Gln Ala Pro Gly Gln Gly Leu Glu Trp
             35                  40                  45

Met Gly Leu Ile Gly Val Gly Ser Gly Ser Leu Trp Tyr Ala Gln Lys
         50                  55                  60

Phe Gln Gly Arg Val Thr Met Thr Arg Asp Thr Ser Thr Ser Thr Val
 65                  70                  75                  80

Tyr Met Glu Leu Ser Ser Leu Arg Ser Glu Asp Thr Ala Val Tyr Tyr
                 85                  90                  95

Cys Ala Arg His Phe Ala Leu Ser Asp Pro Phe Asn Leu Trp Gly Gln
             100                 105                 110

Gly Thr Leu Val Thr Val Ser Ser Ala Ser Thr Lys Gly Pro Ser Val
```

```
            115                 120                 125
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Xaa
    450

<210> SEQ ID NO 12
<211> LENGTH: 1338
<212> TYPE: DNA
<213> ORGANISM: Artificial Sequence
<220> FEATURE:
<223> OTHER INFORMATION: Synthetic Construct

<400> SEQUENCE: 12
caggtgcagc tggtgcagtc tggggctgag gtgaagaagc ctggggcctc agtgaaggtt    60
tcctgcaagg catctggatt ctccttcagt agcggctact acatggcatg ggtgcggcag   120
```

```
gcccctggac aagggcttga gtggatggga ctgattggtg ttggtagtgg tagcctatgg      180
tacgcgcaga agttccaagg ccgggtcacc atgaccaggg acacgtccac gagcacagtc      240
tacatggagc tgagcagcct gagatctgag gacacggccg tgtattactg tgcgagacat      300
tttgctctgt ctgatccctt taacttgtgg ggccagggca cactcgtcac cgtctcctca      360
gctagcacca agggcccatc ggtcttcccc ctggcaccct gctccaggag cacctccgag      420
agcacagccg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacgaagacc      600
tacacctgca acgtagatca caagcccagc aacaccaagg tggacaagag agttgagtcc      660
aaatatggtc ccccatgccc accctgccca gcacctgagt tcctgggggg accatcagtc      720
ttcctgttcc ccccaaaacc caaggacact ctcatgatct cccggacccc tgaggtcacg      780
tgcgtggtgg tggacgtgag ccaggaagac cccgaggtcc agttcaactg gtacgtggat      840
ggcgtggagg tgcataatgc caagacaaag ccgcgggagg agcagttcaa cagcacgtac      900
cgtgtggtca gcgtcctcac cgtcctgcac caggactggc tgaacggcaa ggagtacaag      960
tgcaaggtct ccaacaaagg cctcccgtcc tccatcgaga aaaccatctc caaagccaaa     1020
gggcagcccc gagagccaca ggtgtacacc ctgcccccat cccaggagga tgaccaag      1080 aaccaggtca gcctgacctg cctggtcaaa ggcttctacc ccagcgacat cgccgtggag     1140
tgggaaagca atgggcagcc ggagaacaac tacaagacca cgcctcccgt gctggactcc     1200
gacggctcct tcttcctcta cagcaggcta accgtggaca agagcaggtg gcaggagggg     1260
aatgtcttct catgctccgt gatgcatgag gctctgcaca accactacac acagaagagc     1320 ctctcccctgt ctctgggt                                                  1338
```

<210> SEQ ID NO 13
<211> LENGTH: 645
<212> TYPE: DNA
<213> ORGANISM: Artificial Sequence
<220> FEATURE:
<223> OTHER INFORMATION: Synthetic Construct

<400> SEQUENCE: 13

```
gaaattgtgc tgactcagtc tccagacttt cagtctgtga ctccaaagga gaaagtcacc       60
atcacctgcc aggccagtga gtcgattgat agctatttac tgtggtacca gcagaaacca      120
gatcagtctc caaagctcct catcaagcag gcatccactc tggcatctgg ggtccctcg      180 aggttcagtg gcagtggatc tgggacagat ttcaccctca ccatcaatag cctggaagct      240
gaagatgctg caacgtatta ctgtcaaaac tattatgata ttagtagtaa tgatttcggc      300
ggagggacca aggtggagat caaacggacc gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagactac gagaaacac aaagtctacg cctgcgaagt cacccatcag      600
ggcctgagct cgcccgtcac aaagagcttc aacaggggag agtgc                       645
```

<210> SEQ ID NO 14
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 14

```
caggtgcagc tggtgcagtc tggggctgag gtgaagaagc ctggggcctc agtgaaggtt      60
tcctgcaagg catctggatt ctccttcagt agcggctact acatggcatg ggtgcggcag     120
gcccctggac aagggcttga gtggatggga ctgattggtg ttggtagtgg tagcctatgg     180
tacgcgcaga agttccaagg ccgggtcacc atgaccaggg acacgtccac gagcacagtc     240
tacatggagc tgagcagcct gagatctgag gacacggccg tgtattactg cgagacat      300
tttgctctgt ctgatccctt taacttgtgg ggccagggca cactcgtcac cgtctcctca     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggaccct      780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc catcgagaa aaccatctcc    1020
aaagccaaag gcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaag                                     1350
```

<210> SEQ ID NO 15
<211> LENGTH: 348
<212> TYPE: PRT
<213> ORGANISM: Homo sapiens

<400> SEQUENCE: 15

```
Met Leu Cys Pro Trp Arg Thr Ala Asn Leu Gly Leu Leu Ile Leu
1               5                  10                  15

Thr Ile Phe Leu Val Ala Glu Ala Glu Gly Ala Ala Gln Pro Asn Asn
                20                  25                  30

Ser Leu Met Leu Gln Thr Ser Lys Glu Asn His Ala Leu Ala Ser Ser
            35                  40                  45

Ser Leu Cys Met Asp Glu Lys Gln Ile Thr Gln Asn Tyr Ser Lys Val
        50                  55                  60

Leu Ala Glu Val Asn Thr Ser Trp Pro Val Lys Met Ala Thr Asn Ala
65                  70                  75                  80

Val Leu Cys Cys Pro Pro Ile Ala Leu Arg Asn Leu Ile Ile Thr
                85                  90                  95

Trp Glu Ile Ile Leu Arg Gly Gln Pro Ser Cys Thr Lys Ala Tyr Arg
                100                 105                 110
```

Lys Glu Thr Asn Glu Thr Lys Glu Thr Asn Cys Thr Asp Glu Arg Ile
            115                 120                 125

Thr Trp Val Ser Arg Pro Asp Gln Asn Ser Asp Leu Gln Ile Arg Pro
        130                 135                 140

Val Ala Ile Thr His Asp Gly Tyr Tyr Arg Cys Ile Met Val Thr Pro
145                 150                 155                 160

Asp Gly Asn Phe His Arg Gly Tyr His Leu Gln Val Leu Val Thr Pro
                165                 170                 175

Glu Leu Thr Leu Phe Gln Asn Arg Asn Arg Thr Ala Val Cys Lys Ala
            180                 185                 190

Val Ala Gly Lys Pro Ala Ala Gln Ile Ser Trp Ile Pro Glu Gly Asp
        195                 200                 205

Cys Ala Thr Lys Gln Glu Tyr Trp Ser Asn Gly Thr Val Thr Val Lys
210                 215                 220

Ser Thr Cys His Trp Glu Val His Asn Val Ser Thr Val Thr Cys His
225                 230                 235                 240

Val Ser His Leu Thr Gly Asn Lys Ser Leu Tyr Ile Glu Leu Leu Pro
                245                 250                 255

Val Pro Gly Ala Lys Lys Ser Ala Lys Leu Tyr Ile Pro Tyr Ile Ile
            260                 265                 270

Leu Thr Ile Ile Ile Leu Thr Ile Val Gly Phe Ile Trp Leu Leu Lys
        275                 280                 285

Val Asn Gly Cys Arg Lys Tyr Lys Leu Asn Lys Thr Glu Ser Thr Pro
290                 295                 300

Val Val Glu Glu Asp Glu Met Gln Pro Tyr Ala Ser Tyr Thr Glu Lys
305                 310                 315                 320

Asn Asn Pro Leu Tyr Asp Thr Thr Asn Lys Val Lys Ala Ser Gln Ala
                325                 330                 335

Leu Gln Ser Glu Val Asp Thr Asp Leu His Thr Leu
            340                 345

<210> SEQ ID NO 16
<211> LENGTH: 349
<212> TYPE: PRT
<213> ORGANISM: Macaca fascicularis

<400> SEQUENCE: 16

Met Leu Cys Pro Trp Arg Thr Ala Asn Leu Gly Leu Leu Leu Ile Leu
1               5                   10                  15

Ala Val Phe Leu Val Ala Glu Ala Glu Gly Ala Ala Gln Ser Asn Asn
            20                  25                  30

Ser Leu Met Leu Gln Thr Ser Lys Glu Asn His Thr Leu Ala Ser Asn
        35                  40                  45

Ser Leu Cys Met Asp Glu Lys Gln Ile Thr Gln Asn His Ser Lys Val
50                  55                  60

Leu Ala Glu Val Asn Ile Ser Trp Pro Val Gln Met Ala Arg Asn Ala
65                  70                  75                  80

Val Leu Cys Cys Pro Pro Ile Glu Phe Arg Asn Leu Ile Val Ile Thr
                85                  90                  95

Trp Glu Ile Ile Leu Arg Gly Gln Pro Ser Cys Thr Lys Thr Tyr Arg
            100                 105                 110

Lys Asp Thr Asn Glu Thr Lys Glu Thr Asn Cys Thr Asp Glu Arg Ile
        115                 120                 125

Thr Trp Val Ser Thr Pro Asp Gln Asn Ser Asp Leu Gln Ile His Pro

```
                130                 135                 140
Val Ala Ile Thr His Asp Gly Tyr Tyr Arg Cys Ile Met Ala Thr Pro
145                 150                 155                 160

Asp Gly Asn Phe His Arg Gly Tyr His Leu Gln Val Leu Val Thr Pro
                165                 170                 175

Glu Val Thr Leu Phe Glu Ser Arg Asn Arg Thr Ala Val Cys Lys Ala
            180                 185                 190

Val Ala Gly Lys Pro Ala Ala Gln Ile Ser Trp Ile Pro Ala Gly Asp
        195                 200                 205

Cys Ala Pro Thr Glu Gln Glu Tyr Trp Gly Asn Gly Thr Val Thr Val
    210                 215                 220

Lys Ser Thr Cys His Trp Glu Gly His Asn Val Ser Thr Val Thr Cys
225                 230                 235                 240

His Val Ser His Leu Thr Gly Asn Lys Ser Leu Tyr Ile Glu Leu Leu
                245                 250                 255

Pro Val Pro Gly Ala Lys Lys Ser Ala Lys Leu Tyr Met Pro Tyr Val
            260                 265                 270

Ile Leu Thr Ile Ile Ile Leu Thr Ile Val Gly Phe Ile Trp Leu Leu
        275                 280                 285

Lys Ile Ser Gly Cys Arg Lys Tyr Asn Leu Asn Lys Thr Glu Ser Thr
    290                 295                 300

Ser Val Val Glu Glu Asp Glu Met Gln Pro Tyr Ala Ser Tyr Thr Glu
305                 310                 315                 320

Lys Asn Asn Pro Leu Tyr Asp Thr Thr Asn Lys Val Lys Ala Ser Gln
                325                 330                 335

Ala Leu Gln Ser Glu Val Gly Thr Asp Leu His Thr Leu
            340                 345

<210> SEQ ID NO 17
<211> LENGTH: 278
<212> TYPE: PRT
<213> ORGANISM: Macaca fascicularis

<400> SEQUENCE: 17

Met His Thr Leu Gly Lys Met Ser Ala Ser Arg Leu Leu Ile Ser Ile
1               5                   10                  15

Ile Ile Met Val Ser Ala Ser Ser Ser Cys Met Asp Gly Lys Gln
            20                  25                  30

Met Thr Gln Asn Tyr Ser Lys Met Ser Ala Glu Gly Asn Ile Ser Gln
        35                  40                  45

Pro Val Leu Met Asp Thr Asn Ala Met Leu Cys Cys Pro Pro Ile Glu
    50                  55                  60

Phe Arg Asn Leu Ile Val Ile Val Trp Glu Ile Ile Arg Gly Gln
65                  70                  75                  80

Pro Ser Cys Thr Lys Ala Tyr Arg Lys Glu Thr Asn Glu Thr Lys Glu
                85                  90                  95

Thr Asn Cys Thr Asp Glu Arg Ile Thr Trp Val Ser Thr Pro Asp Gln
            100                 105                 110

Asn Ser Asp Leu Gln Ile His Pro Val Ala Ile Thr His Asp Gly Tyr
        115                 120                 125

Tyr Arg Cys Ile Met Ala Thr Pro Asp Gly Asn Phe His Arg Gly Tyr
    130                 135                 140

His Leu Gln Val Leu Val Thr Pro Glu Val Thr Leu Phe Gln Ser Arg
145                 150                 155                 160
```

-continued

```
Asn Arg Thr Ala Val Cys Lys Ala Val Ala Gly Lys Pro Ala Ala Gln
            165             170             175

Ile Ser Trp Ile Pro Ala Gly Asp Cys Ala Pro Thr Glu His Glu Tyr
            180             185             190

Trp Gly Asn Gly Thr Val Thr Val Glu Ser Met Cys His Trp Gly Asp
        195             200             205

His Asn Ala Ser Thr Met Thr Cys His Val Ser His Leu Thr Gly Asn
    210             215             220

Lys Ser Leu Tyr Ile Lys Leu Asn Ser Gly Leu Arg Thr Ser Gly Ser
225             230             235             240

Pro Ala Leu Asp Leu Leu Ile Ile Leu Tyr Val Lys Leu Ser Leu Phe
            245             250             255

Val Val Ile Leu Val Thr Thr Gly Phe Val Phe Phe Gln Arg Ile Asn
            260             265             270

Tyr Val Arg Lys Ser Leu
            275
```